(12) United States Patent
Whitman et al.

(10) Patent No.: US 8,132,704 B2
(45) Date of Patent: Mar. 13, 2012

(54) SURGICAL DEVICE

(75) Inventors: Michael P. Whitman, New Hope, PA (US); Peter T. Datcuk, Glenside, PA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/835,807

(22) Filed: Jul. 14, 2010

(65) Prior Publication Data

US 2010/0276470 A1 Nov. 4, 2010

Related U.S. Application Data

(63) Continuation of application No. 11/191,665, filed on Jul. 27, 2005, now Pat. No. 7,770,773.

(51) Int. Cl.
*A61B 17/28* (2006.01)
*A61B 17/285* (2006.01)
*A61B 17/068* (2006.01)

(52) U.S. Cl. ............... 227/175.1; 227/180.1; 227/181.1; 606/139; 606/219; 128/898; 81/424; 269/6

(58) Field of Classification Search ............... 227/175.1, 227/180.1, 181.1; 606/139, 219; 128/898; 81/424; 269/6
See application file for complete search history.

(56) References Cited

U.S. PATENT DOCUMENTS

| | | | |
|---|---|---|---|
| 4,485,811 A | 12/1984 | Chernousov et al. | |
| 5,255,579 A * | 10/1993 | Fortin | 81/424 |
| 5,653,374 A | 8/1997 | Young et al. | |
| 5,667,517 A | 9/1997 | Hooven | |
| 5,732,871 A | 3/1998 | Clark et al. | |
| 5,779,130 A | 7/1998 | Alesi et al. | |
| 5,797,959 A | 8/1998 | Casiro et al. | |
| 6,119,913 A | 9/2000 | Adams et al. | |
| 6,270,508 B1 | 8/2001 | Klieman et al. | |
| 6,517,565 B1 * | 2/2003 | Whitman et al. | 606/219 |
| 6,843,403 B2 | 1/2005 | Whitman | |
| 2001/0031975 A1 | 10/2001 | Whitman et al. | |
| 2002/0188320 A1 | 12/2002 | Fuchs et al. | |
| 2003/0130677 A1 | 7/2003 | Whitman et al. | |

FOREIGN PATENT DOCUMENTS

WO WO 00/72765 12/2000
WO WO 01/03587 1/2001

OTHER PUBLICATIONS

International Search Report corresponding to PCT Application No. PCT/US2006/029285, date of mailing is Sep. 12, 2007; date of completion is Jul. 18, 2007; (2 pages).
Extended European Search Report for EP 10 01 2644, dated Mar. 3, 2011.

* cited by examiner

*Primary Examiner* — Thanh K Truong
*Assistant Examiner* — Michelle Lopez

(57) ABSTRACT

A surgical device includes a first jaw and a second jaw moveable relative to the first jaw between a first position, in which the first and second jaws are aligned within a plane, and a second position, in which the second jaw is in non-parallel correspondence to the plane. The surgical device may include a surgical member, e.g., a cutting and/or stapling element, disposed within the first jaw, and a second driver configured to cause relative movement of the surgical member in a direction parallel to the plane. The first and second jaws may include a camming arrangement that is configured to move the second jaw between the first and second positions. The camming arrangement may include a channel disposed along at least a portion of one or both of the first and second jaws, a ball bearing disposed within the channel.

43 Claims, 18 Drawing Sheets

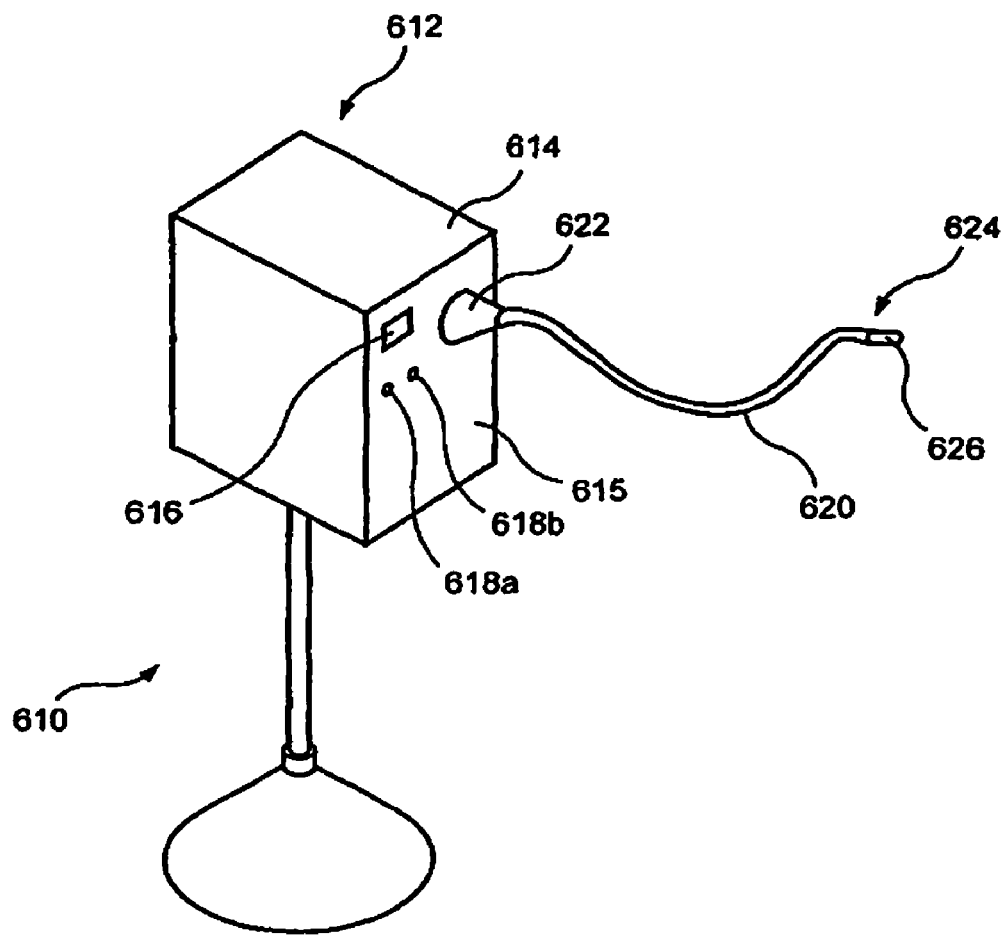
F I G. 2

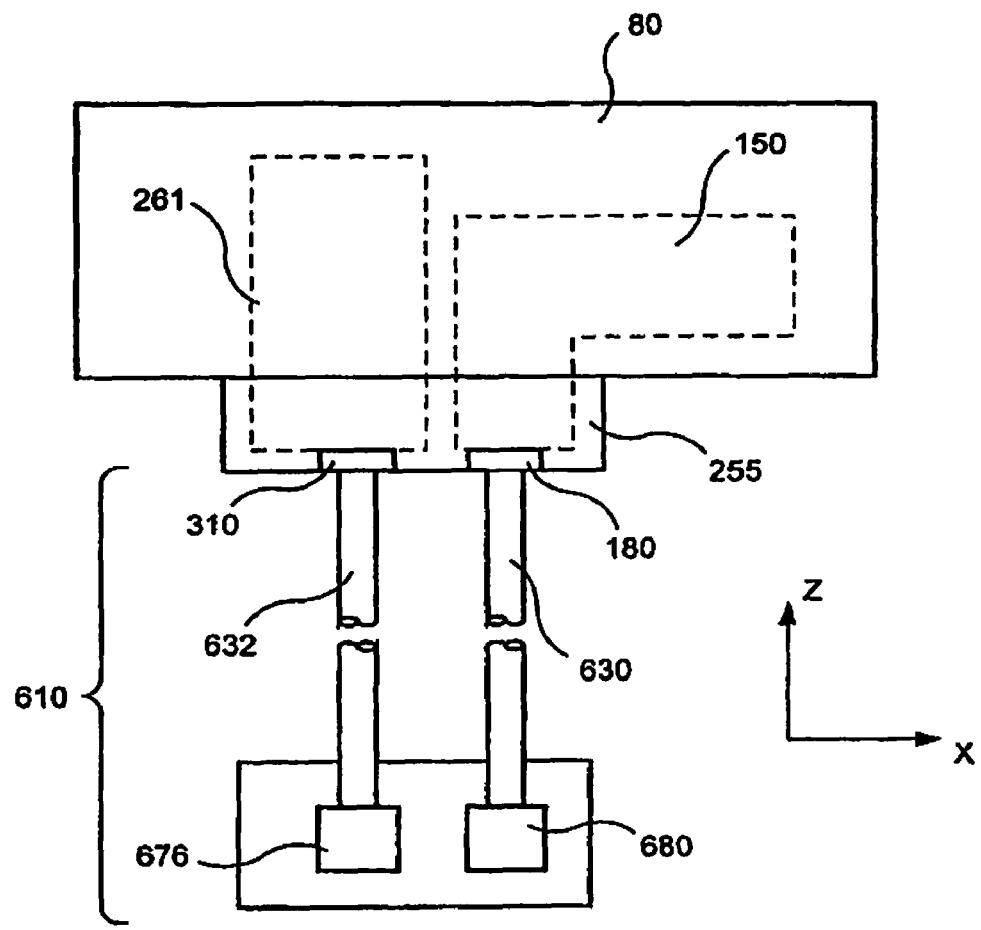
F I G. 7

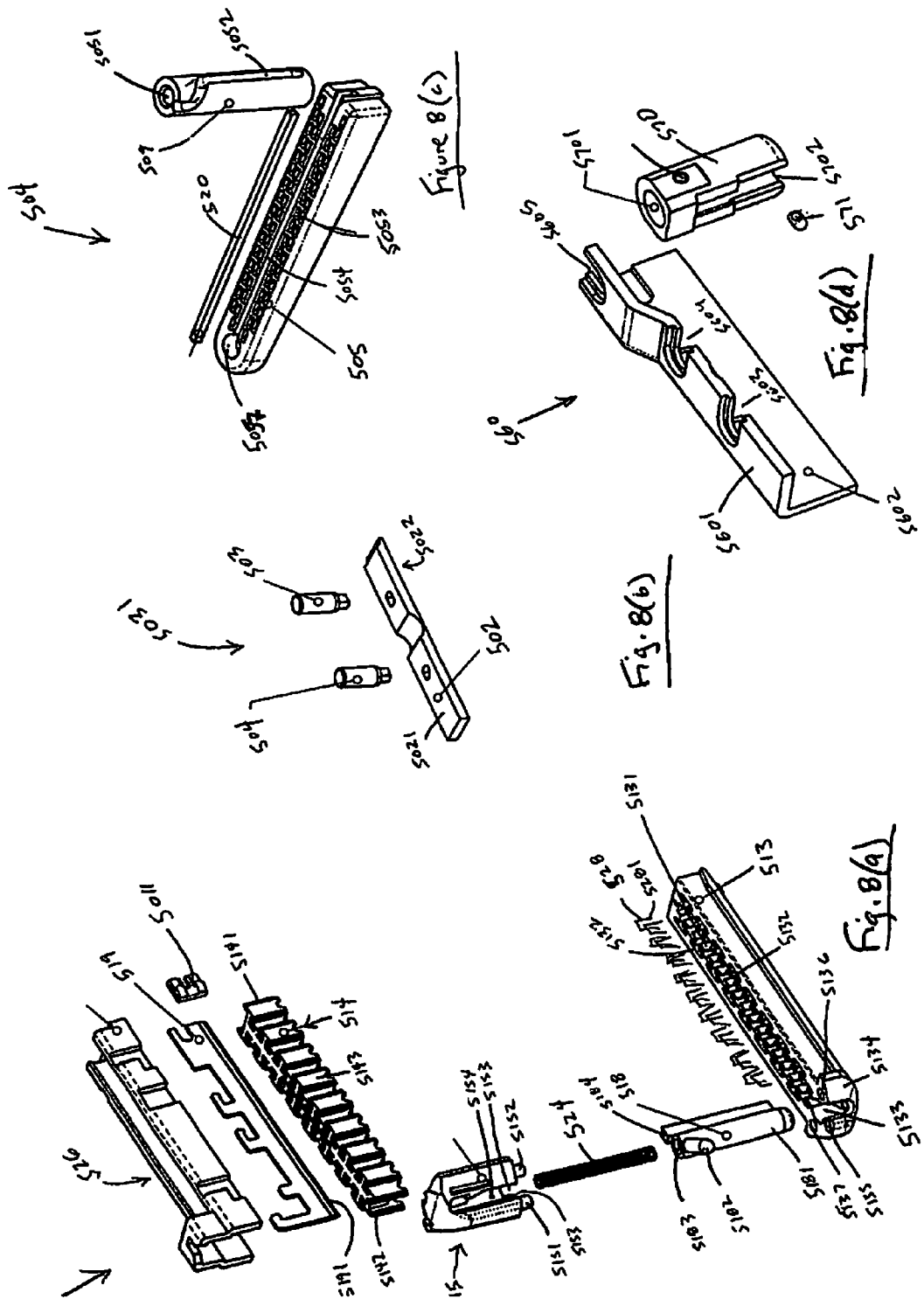

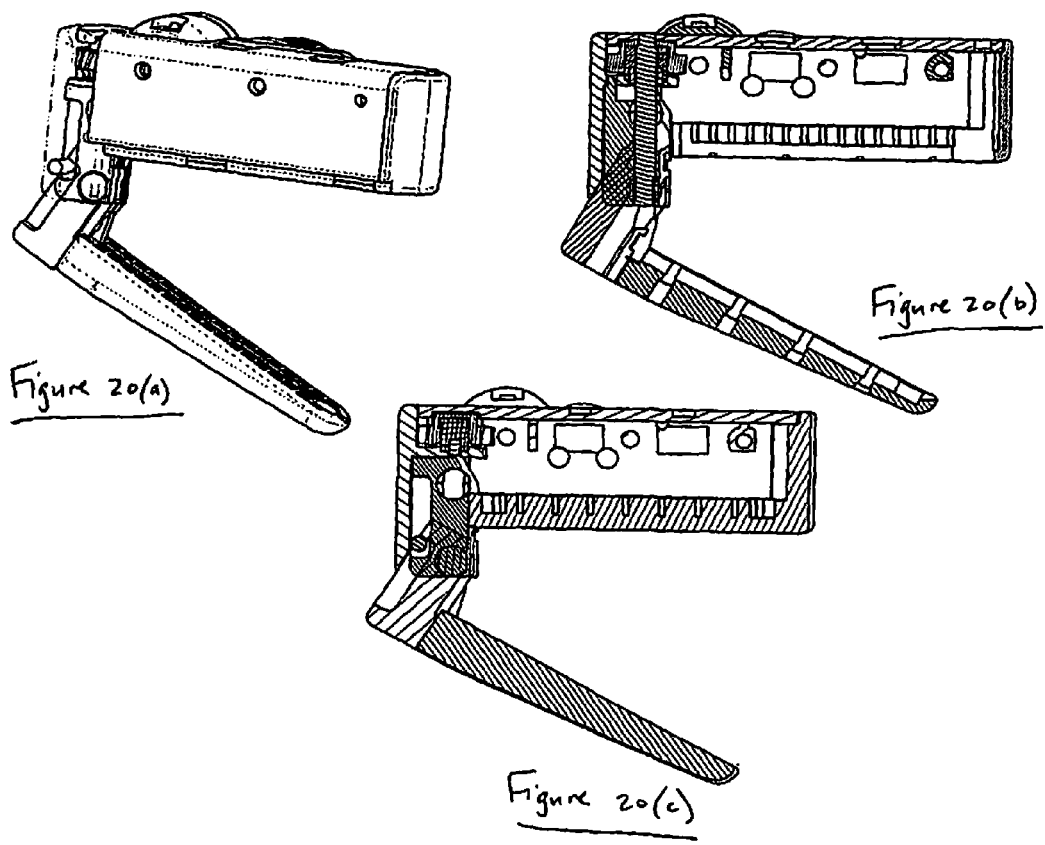

SURGICAL DEVICE

CROSS-REFERENCE TO RELATED APPLICATIONS

The present application is a Continuation Application which claims the benefit of and priority to U.S. application Ser. No. 11/191,665, filed on Jul. 27, 2005, the entire content of which is expressly incorporated herein by reference in its entirety.

The present application is related to U.S. patent application Ser. No. 09/510,923, filed on Feb. 22, 2000, now issued as U.S. Pat. No. 6,517,565 on Feb. 11, 2003, U.S. patent application Ser. No. 09/723,715, filed on Nov. 28, 2000, now issued as U.S. Pat. No. 6,793,652 on Sep. 21, 2004, U.S. patent application Ser. No. 09/836,781, filed on Apr. 17, 2001, now issued as U.S. Pat. No. 6,981,941 on Jan. 3, 2006, U.S. patent application Ser. No. 09/887,789, filed on Jun. 22, 2001, now issued as U.S. Pat. No. 7,032,798 on Apr. 25, 2006, and U.S. Provisional Patent Application Ser. No. 60/337,544, filed on Dec. 4, 2001, U.S. patent application Ser. No. 10/309,532, filed on Dec. 4, 2002, U.S. patent application Ser. No. 10/094,051, filed on Mar. 8, 2002, each of which is expressly incorporated herein by reference in its entirety.

FIELD OF THE INVENTION

The present invention relates to a surgical device. More specifically, the present invention relates to a clamping, cutting and stapling device having a swivelable jaw.

BACKGROUND INFORMATION

The literature is replete with descriptions of surgical devices. Some of these surgical devices are described in U.S. Pat. No. 4,705,038 to Sjostrom et al.; U.S. Pat. No. 4,995,877 to Ams et al.; U.S. Pat. No. 5,249,583 to Mallaby; U.S. Pat. No. 5,395,033 to Byrne et al.; U.S. Pat. No. 5,467,911 to Tsuruta et al.; U.S. Pat. Nos. 5,383,880, 5,518,163, 5,518,164 and 5,667,517, all to Hooven; U.S. Pat. No. 5,653,374 to Young et al.; U.S. Pat. No. 5,779,130 to Alesi et al.; and U.S. Pat. No. 5,954,259 to Viola et al.

One type of surgical device is a straight stapling device, which is a guillotine-type device that is used to cut and staple a section of tissue. FIG. 1(a) illustrates an example of such a device as described in U.S. Pat. No. 3,494,533. The device illustrated in FIG. 1(a) includes opposing jaws that move in parallel correspondence to each other. A first jaw has disposed therein an arrangement of staples while the second jaw provides an anvil for receiving and closing the staples. A staple pusher is located within the first jaw and extends from a proximal end of the first jaw to a distal end of the first jaw. A drive shaft, coupled to the first jaw and to the staple pusher, is located in the plane of movement of the first jaw and the staple pusher. When actuated, the drive shaft drives the staple pusher so as to simultaneously push all of the staples against the staple guides in the anvil of the second jaw.

Other examples of surgical devices are described in U.S. Pat. No. 4,442,964, U.S. Pat. No. 4,671,445, and U.S. Pat. No. 5,413,267. Such surgical staplers include opposing jaws that move in parallel correspondence to each other, wherein a first jaw has disposed therein an arrangement of staples while the second jaw provides an anvil for receiving and closing the staples. A staple pusher is located within the first jaw and that extends from a proximal end of the first jaw to a distal end of the first jaw. A drive shaft, coupled to the first jaw and to the staple pusher, is located in the plane of movement of the first jaw and the staple pusher and when actuated, the drive shaft drives the staple pusher so as to simultaneously push all of the staples against the staple guides in the anvil of the second jaw.

Another type of surgical device is a linear clamping, cutting and stapling device, such as that described in U.S. Pat. No. 6,264,087. Such a device may be employed in a surgical procedure to resect a cancerous or anomalous tissue from a gastro-intestinal tract. A conventional linear clamping, cutting and stapling instrument is illustrated in a perspective view in FIG. 1(b). The device includes a pistol grip-styled structure having an elongated shaft and distal portion. The distal portion includes a pair of scissors-styled gripping elements, which clamp the open ends of the colon closed. One of the two scissors-styled gripping elements, the anvil portion, moves or pivots relative to the overall structure, whereas the other gripping element remains fixed relative to the overall structure. The actuation of this scissoring device, i.e., the pivoting of the anvil portion, is controlled by a grip trigger arranged in the handle. In addition to the scissoring device, the distal portion also includes a stapling mechanism. The fixed gripping element of the scissoring mechanism includes a staple cartridge receiving region and a mechanism for driving the staples through the clamped end of the tissue, against the anvil portion, thereby sealing the previously opened end. The scissoring elements may be integrally formed with the shaft or may be detachable such that various scissoring and stapling elements may be interchangeable.

Generally, these surgical devices are employed in the following manner: upon identification of cancerous or other anomalous tissue in the gastrointestinal tract (and upon determination that the cancerous tissue is located at a position in the colon), a patient's abdomen is initially opened to expose the bowel. A surgeon then cuts the tube of the colon on either side of the cancerous tissue, and staples closed the two open ends of the bowel (a distal end which is directed toward the anus, and the proximal end which is closest to the lower intestine). This temporary closure is performed in order to minimize contamination of the exposed abdomen by the bowel contents. More particularly, this temporary closure of the two open ends of the bowel is achieved when the colon is placed between the jaws of the surgical device. By actuating a first driving mechanism, the surgeon causes the jaws to come together. A second driving mechanism is then actuated to drive a series of staples and a cutting blade through the clamped end of the colon, thereby closing and transecting the ends. This procedure is typically repeated a second time on the other side of the cancerous or anomalous tissue.

One problem with the foregoing surgical devices is that the devices may be difficult to maneuver. Because these devices may be employed corporally, e.g., inside the body of a patient, the device should be configured so as to be maneuverable inside the body of a patient. Conventional surgical devices, such as those illustrated in FIGS. 1(a) and 1(b), are difficult to maneuver, especially inside the patient's body.

Another problem with the foregoing surgical devices is that the devices may not be positionable satisfactorily within the patient's body. For example, when a conventional device is employed to clamp, cut and staple a section of tissue immediately adjacent to an anal stump, it may be desirable to position the device, and to clamp, cut and staple a section of tissue, as close as possible to the anus—however, conventional devices may not be positionable as close to the anal stump as desired because the jaws of the surgical device, when in the open position, require a large space and are prevented from being satisfactorily positioned by tissue inside the patient's body and surrounding the anal stump.

SUMMARY OF THE INVENTION

The present invention, according to one example embodiment thereof, relates to a surgical device. The surgical device includes a first jaw. The surgical device also includes a second jaw moveable relative to the first jaw between a first position, in which the first and second jaws are aligned within a plane, and a second position, in which the second jaw is in non-parallel correspondence to the plane. In this manner, the second jaw is moveable, e.g., swivelable, relative to the first jaw between a closed position and an open position. For instance, during operation, the second jaw may move within the plane as the second jaw is moved a first distance relative to the first jaw, and may move at least partially out of the plane, e.g., may swivel, as the second jaw is moved a second distance relative to the first jaw. The surgical device may include a first driver configured to cause relative movement of the first jaw and the second jaw, the first driver being configured to engage a drive shaft rotatable about a rotation axis arranged in either parallel or non-parallel, e.g., perpendicular, correspondence to the plane.

The surgical device may also includes a surgical member, e.g., a cutting and/or stapling element, disposed within the first jaw, and a second driver configured to cause relative movement of the surgical member in a direction parallel to the plane. The second driver may be configured to engage a second drive shaft rotatable about a rotation axis arranged in either a parallel or non-parallel, e.g., perpendicular, correspondence to the plane. An electro-mechanical driver may be employed to rotate the first rotatable drive shaft, such that the first rotatable drive shaft is rotated in a first direction to effect extending of the jaws and rotated in a second direction opposite to the first direction to effect closing of the jaws. In one embodiment, the first driver includes at least a spur gears, a worm and a worm gear in turning and gearing relationship with each other, and an externally-threaded screw fixedly connected at one end to the worm gear and in engagement with an internally-threaded bore of the second jaw, the rotation of the gears thereby causing relative movement of the first jaw and the second jaw.

In addition, the electro-mechanical driver may be employed to rotate the second rotatable drive shaft, such that the second rotatable drive shaft is rotated in a first direction to extend the surgical member and rotated in a second direction opposite to the first direction to retract the surgical member. In one embodiment, the second driver includes at least a spur gear and a worm in turning and gearing relationship with each other and with a pair of additional worm gears, each of the pair of additional worm gears having a centrally-disposed, internally-threaded bore in engagement with one of a pair of externally-threaded screws fixedly connected the surgical member, the rotation of the gears thereby causing relative movement of the surgical member. The electro-mechanical driver may include at least one motor arrangement adapted to drive each of the first and second rotatable drive shafts.

In one embodiment, the internally threaded bore of the second jaw is disposed within an arm, the arm configured to move longitudinally within and relative to a sleeve attached to the first jaw, the sleeve and the arm having a camming arrangement that configured to move the second jaw between the first and second positions. The camming arrangement may include a channel disposed along at least one of the arm and the sleeve, a ball bearing disposed within the channel.

The present invention, according to one example embodiment thereof, relates to a surgical device including a first jaw and a second jaw. The second jaw is coupled to and moveable relative to the first jaw between a closed position and an intermediate open position. Between the closed position and the intermediate open position, the clamping surfaces of the first and second jaws define first and second planes that remain in parallel correspondence relative to each other. In addition, the second jaw is further moveable relative to the first jaw between the intermediate open position and a fully opened position. Between the intermediate open position and the fully opened position, the first and second planes defined by the clamping surfaces of the first and second jaws are moved out of parallel correspondence relative to each other. For instance, between the intermediate open position and a fully opened position, the second jaw may be pivotable relative to the first jaw about an axis perpendicular to the plane. In the closed position, the first jaw and the second jaw may be arranged in a third plane, and a first driver configured to cause relative movement of the first jaw and the second jaw may be configured to engage a first rotatable drive shaft that is rotatable about a rotation axis arranged in one of parallel and non-parallel correspondence to the third plane. The surgical device may also include a surgical member, e.g., a cutting and/or stapling element or a thrust plate to which is mounted a cutting and/or stapling element, the surgical member being disposed within the first jaw, wherein a second driver is configured to cause relative movement of the surgical member in a direction parallel to the third plane. The second driver may engage a second drive shaft rotatable about a rotation axis arranged in one of parallel and non-parallel correspondence to the third plane. An electro-mechanical driver may be employed to rotate the first and/or second rotatable drive shafts.

BRIEF DESCRIPTION OF THE DRAWINGS

FIG. 1(*b*) is a perspective view of a conventional linear clamping, cutting and stapling device;

FIG. 2 is a perspective view of an electro-mechanical surgical system according to one example embodiment of the present invention;

FIG. 7 is a top view of the cutting and stapling attachment illustrated in FIGS. 3 and 4;

FIG. 8(*b*) is an exploded view of a thrust plate component, according to another example embodiment of the present invention;

FIG. 8(*c*) is an exploded view of an anvil component, according to one example embodiment of the present invention;

FIG. 8(*d*) is an exploded view of a side plate component, according to another example embodiment of the present invention;

FIG. 8(*e*) is a partially exploded perspective view of the cutting and stapling attachment, according to another example embodiment of the present invention;

FIGS. 20(*a*)-(*c*) are various views of a cutting and stapling attachment according to another example embodiment of the present invention.

DETAILED DESCRIPTION

Figure 1A:
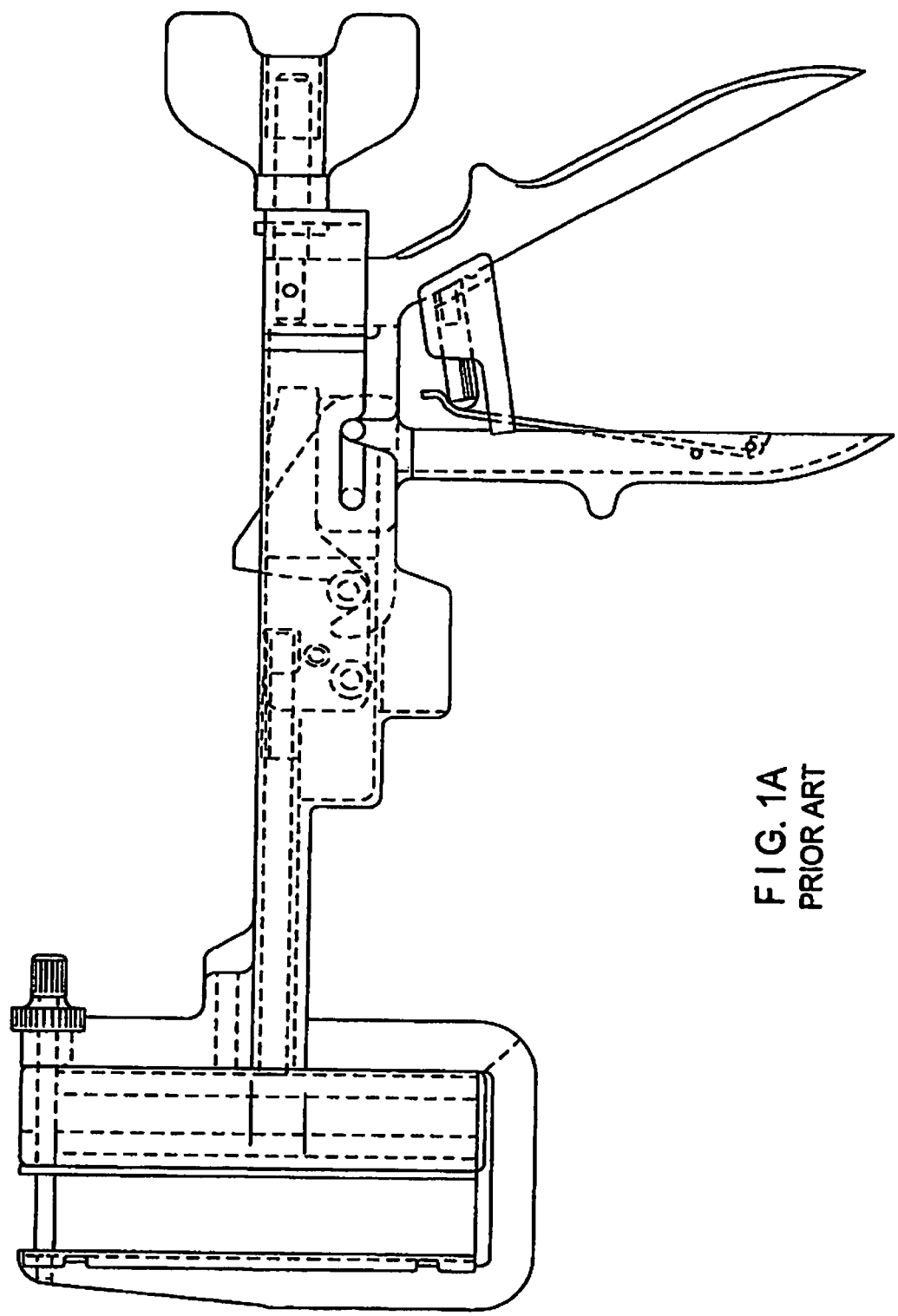
FIG. 1(*a*) is a side view of a conventional surgical device.
Figure 1B:
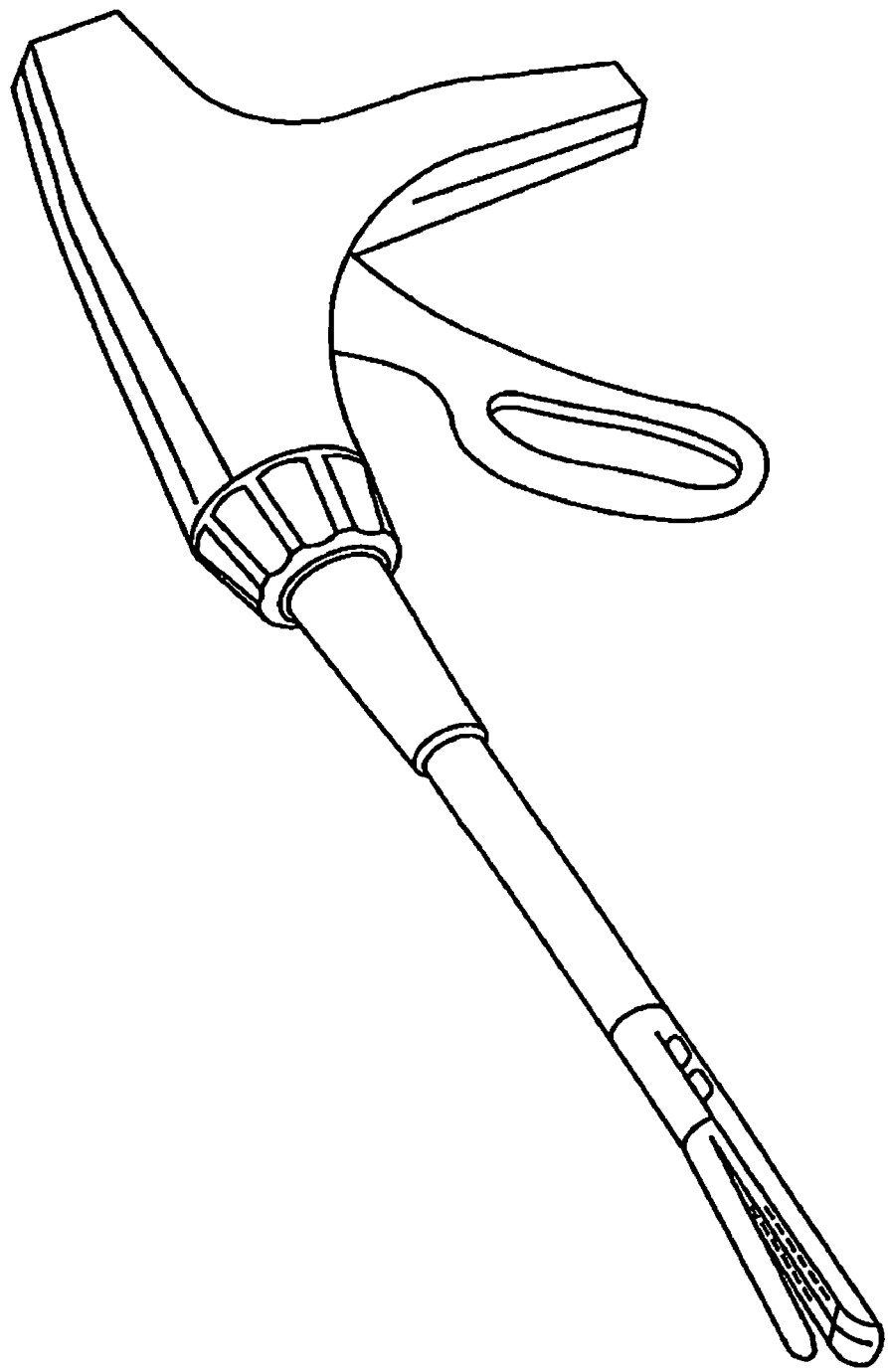
Figures 3, 4:
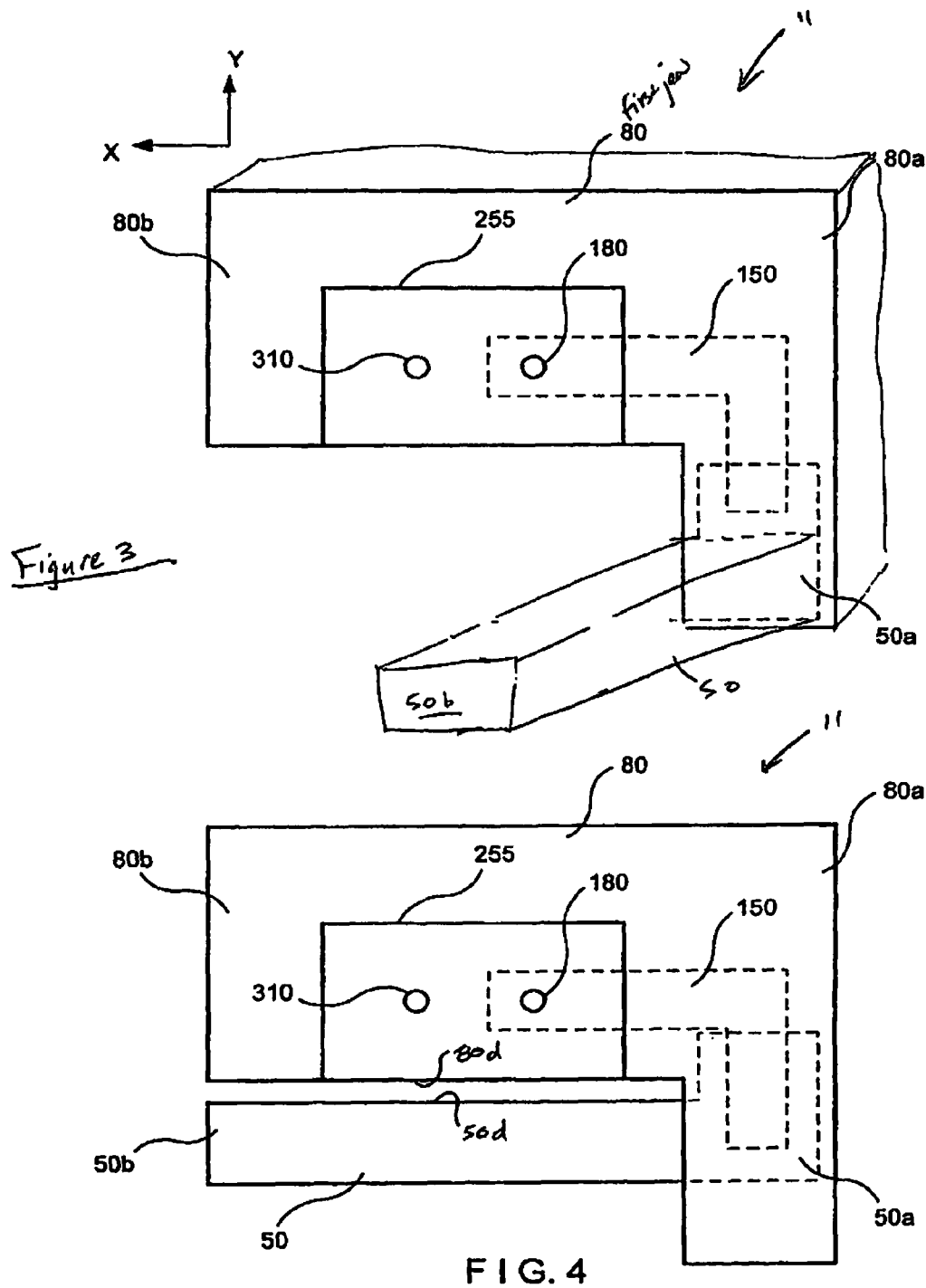
FIG. 3 is a perspective view of a cutting and stapling attachment according to one example embodiment of the present invention in an open position.
FIG. 4 is a side view of the cutting and stapling attachment illustrated in FIG. 3 in a closed position.

An example embodiment of a surgical device 11 according to the present invention is illustrated in FIGS. 3 to 7. Referring to FIGS. 3 and 4, an example embodiment of the surgical device 11, e.g., a clamping, cutting and stapling device, is illustrated. In this example embodiment, the surgical device 11 includes a second jaw 50 moveable relative to a first jaw 80. A first end 50*a* of second jaw 50 is mechanically coupled to a first end 80*a* of first jaw 80.

FIG. 3 is a perspective view that illustrates the surgical device 11 in an open position, wherein the second jaw 50 and the first jaw 80 are in contact with each other at their first ends 50*a* and 80*a*. In the open position, the first jaw 80 is maintained in a longitudinal plane defined by the x and y axes illustrated in FIG. 3, while the second jaw 50 is moved, e.g., swiveled, at least partially out of the longitudinal plane defined by the x and y axes. Specifically, the surgical device 11 is configured such that, in addition to the second jaw 50 moving vertically relative to the first jaw 80, the distal end 50*b* of the second jaw 50 moves into and out of alignment with the distal end 80*b* of the first jaw 80*b*.

Mounted on a side of the first jaw 80*a* is a gear housing 255. The gear housing 255 includes a first drive socket 180 coupled to a first driver 150, which for purposes of clarity is illustrated schematically. The first driver 150 is coupled to a first end 50*a* of the second jaw 50 to open and close the first jaw 80 and the second jaw 50. In addition, the gear housing 255 also includes a second drive socket 310.

FIG. 4 illustrates the surgical device 11 in a closed position. In the closed position, the second jaw 50 and the first jaw 80 are in contact with each other at their first ends 50*a* and 80*a* and also at their second ends 50*a* and 50*b*. Thus, between the open and closed positions illustrated in FIGS. 3 and 4, respectively, the distal end 50*b* of the second jaw 50 is moved into alignment with the distal end 80*b* of the first jaw 80*b*. In the closed position, a section of tissue may be clamped between the second jaw 50 and the first jaw 80.

Figure 5:
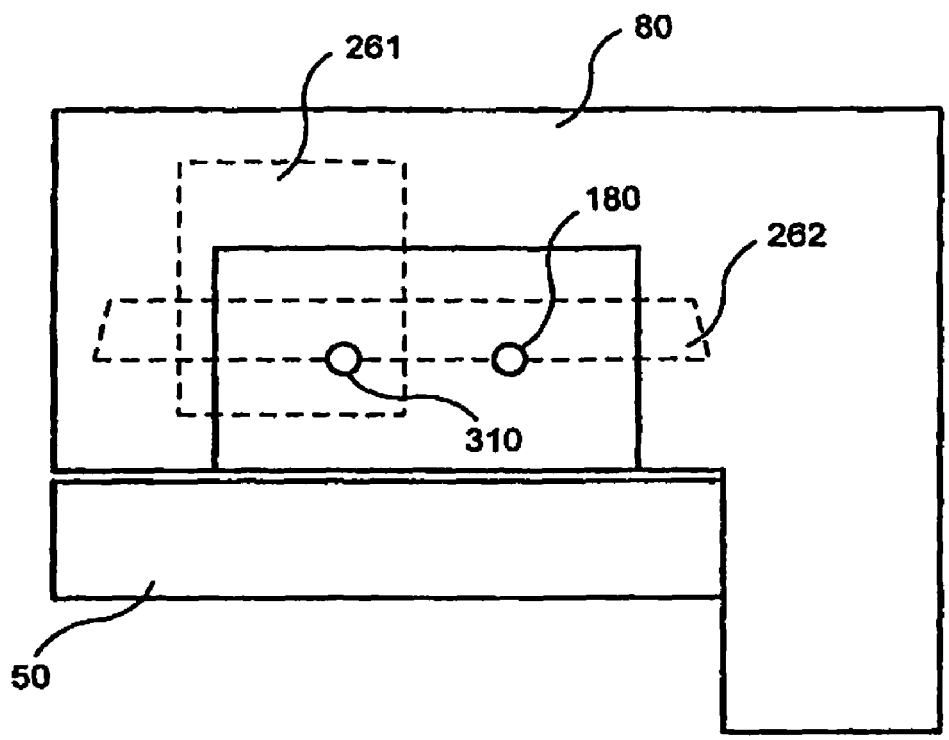
FIG. 5 is a side view of the cutting and stapling attachment illustrated in FIGS. 3 and 4 having a surgical element in the retracted position.
Figure 6:
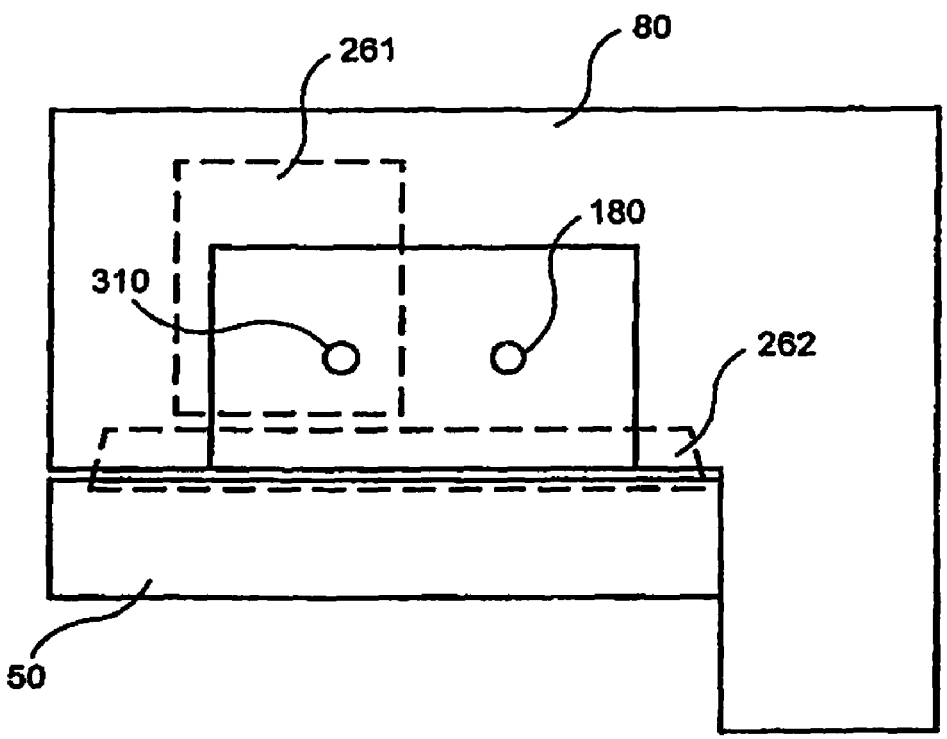
FIG. 6 is a side view of the cutting and stapling attachment illustrated in FIGS. 3 to 5 having the surgical elements in the extended position.

FIGS. 5 and 6 also illustrate the surgical device 11 in the closed position. FIGS. 5 and 6 illustrate the second drive socket 310 of the gear housing 255 coupled to a second driver 261, which is illustrated schematically. The second driver 261 is coupled to a surgical member 262. The surgical member 262 may include a cutting and stapling assembly 262, although other types of surgical members may be provided.

The second driver 261 is coupled to cutting and stapling assembly 262 to move the cutting and stapling assembly 262 from a first retracted position, as illustrated in FIG. 5, to a second extended position, as illustrated in FIG. 6. While two drive sockets, e.g., the first drive socket 180 and the second drive socket 310, and two corresponding drive shafts, e.g., the first drive shaft 630 and the second drive shaft 632 (see below), are illustrated, it is possible to provide any suitable number of drive sockets and drive shafts. For example, a single drive shaft may be provided to drive the surgical device.

FIG. 7 is a top view of the surgical device 11 illustrated in FIGS. 3 to 6. FIG. 7 illustrates the surgical device 11 coupled, e.g., removably or permanently, to an electro-mechanical driver component 610. FIG. 7 illustrates the surgical device 11 including the first driver 150, which is coupled via first drive socket 180 to a first motor 680 of the system 610 by a first drive shaft 630. The first driver 150, when engaged by system 610, operates to open and close the first jaw 80 relative to the second jaw 50. In addition, FIG. 7 illustrates the surgical device 11 including a second driver 261, which is coupled via the second drive socket 310 to a second motor 676 of system 610 by a second drive shaft 632. The second driver 261, when engaged by the system 610, operates to drive a cutting and stapling assembly 262. As illustrated in FIG. 7, the first drive socket 180 and the second drive socket 310 are disposed on the surgical device 11 so that the first drive shaft 630 and the second drive shaft 632 may be coupled to the surgical device 11 at an angle, e.g., perpendicularly, to the x-y plane illustrated in FIG. 3. That is, the first drive shaft 630 and the second drive shaft 632 may be coupled to the surgical device 11, e.g., in the direction of the z-axis illustrated in FIG. 7.

Figure 8C:
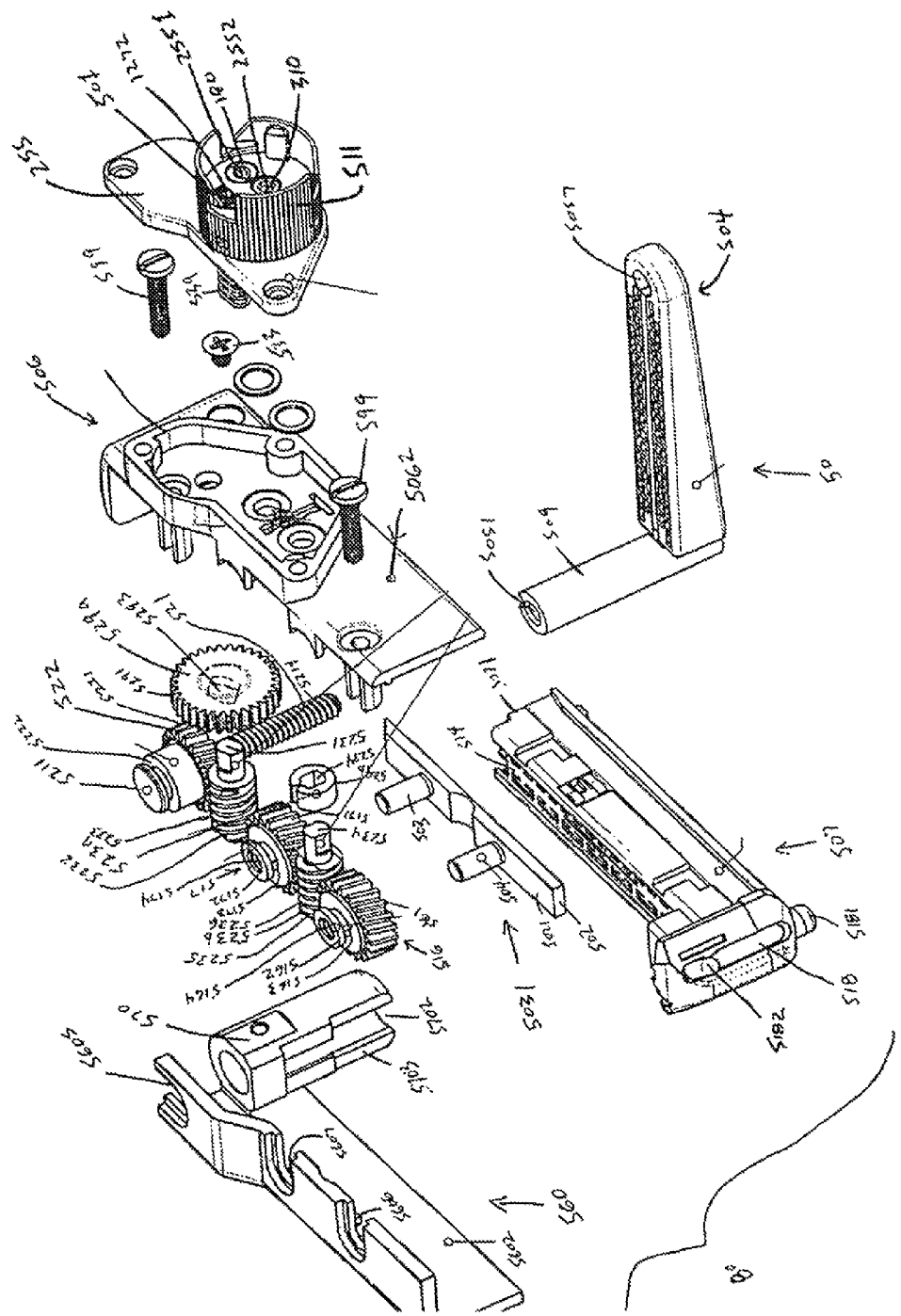
FIG. 8(*a*) is an exploded view of a staple cartridge assembly, according to one example embodiment of the present invention.
Figure 9:
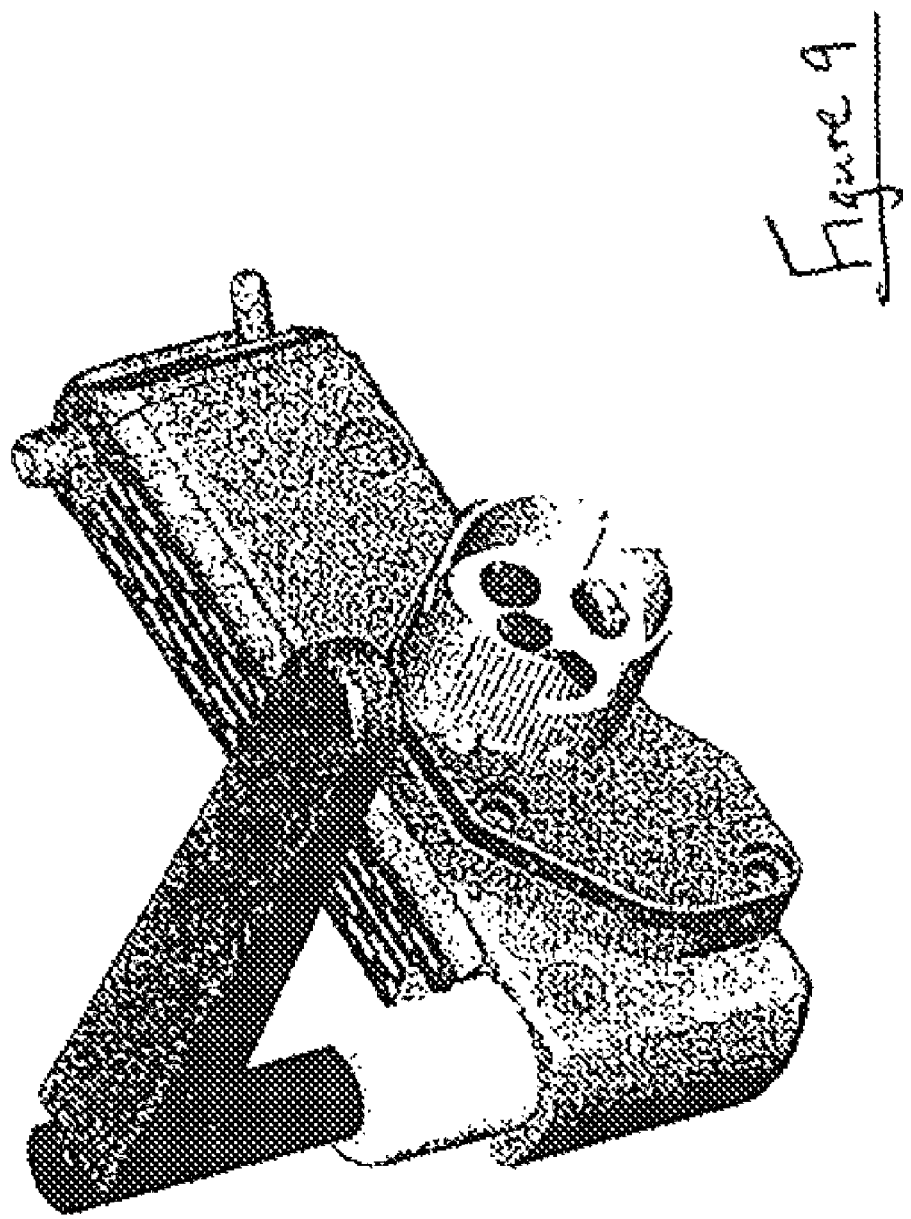
FIG. 9 is an assembled, perspective view of the cutting and stapling attachment illustrated in FIGS. 8(*a*) through 8(*e*) in the open position.

FIGS. 8(*a*) through 8(*e*) are various exploded views of the surgical device 11 according to an example embodiment of the present invention, and FIG. 9 is a perspective view of the surgical device 11 assembled.

FIG. 8(*a*) is an exploded view of a staple cartridge assembly 507. The staple cartridge assembly 507 includes a staple pusher 514. The staple pusher 514 is attached to a bottom surface 5022 of a thrust plate 502 (explained below). The staple pusher 514 includes parallel rows 5141 and 5142 of downwardly-disposed teeth 5143, each of which corresponds to and aligns with a staple guide 5053 of the anvil 505 (explained below). A knife 519 having a cutting edge 5191 facing downwardly is disposed between the parallel rows of downwardly-disposed teeth 5143 of the staple pusher 514.

A staple holder 513 is disposed below the staple pusher 514. The staple holder 513 includes a cartridge having vertically-disposed slots 5132, each of which corresponds to and aligns with the downwardly-disposed teeth 5143 of the staple pusher 514 and with the staple guides 5053 of the anvil 505. A staple 528, which includes prongs 5281, is provided in each slot 5132. The staple holder 513 also includes a longitudinally-disposed slot 5131, which extends through the staple holder 513 and through which knife 519 may be passed. The staple holder 513 includes a hole 5133 adjacent to one end 5134.

The hole 5133 of the staple holder 513 that is adjacent to the one end 5134 of the staple holder 513 is configured to receive an end 5181 of a pin 518. In the example embodiment, the pin 518 is maintained in a substantially vertical position so as to be perpendicular to the staple holder 513. The pin 518 includes a centrally-disposed internal bore 5183 at its opposite end 5184 configured to receive a spring 524. Also located at the end 5184 of the pin 518 is a lever 5182 which is attached perpendicularly to the pin 518. The spring 524 biases the end 5181 of the pin 518 into an orifice 5057 of an anvil 505 (explained below).

A cartridge cap 515 is attached, such as by welding, to the end 5134 of the staple holder 513. Pins 5151, 5152 and 5153 of the cartridge cap 515 engage openings 5135, 5136 and 5137, respectively, of the staple holder 513. The cartridge cap 515 also includes an internally-disposed bore 5154 which is configured to receive pin 518. The bore 5154 of the cartridge cap 515 includes a slot 5153 in communication therewith, the slot 5153 configured to guide the lever 5182 of the pin 518. In an example embodiment, the internally-disposed bore 5154 of the cartridge cap 515 does not extend through the top surface 5155 of the cartridge cap 515; instead, it maintains the spring 524 within the internally-disposed bore 5154. The biasing force of the spring 524 pushes the end 5181 of the pin 518 into the hole 5133 of the staple holder 513 and tends to ensure that the staple holder 513 is positioned so that the slots 5132 align with the downwardly-disposed teeth 5143 of the staple pusher 514 and with the staple guides 5053 of the anvil 505. The cartridge cap 515 is also maintained in position by a staple cartridge sleeve 526, which covers the staple holder 513. Within a slot 5261 of the staple cartridge sleeve in mounted a memory unit 5011.

FIG. 8(b) is an exploded view of a thrust plate component 5031. The thrust plate component 5031 includes screws 503 and 504. Both the screws 503 and 504 are fixedly coupled, e.g., by welding, to a top surface 5021 of a thrust plate 502.

FIG. 8(c) is an exploded view of an anvil component 504. According to this example embodiment, the anvil component 504 includes an anvil 505, which is coupled, e.g., by welding, to an anvil swivel arm 509. The anvil swivel arm 509 includes a vertically-disposed, internally-threaded bore 5051 extending longitudinally therethrough. The anvil swivel arm 509 also includes a camming arrangement, e.g., a channel 5052 on its outer surface. The channel 5052 extends longitudinally along a lower portion of the outer surface of the anvil swivel arm 509, and then curves as shown in FIG. 8(c) along an upper portion of the outer surface of the anvil swivel arm 509. In addition, the anvil 505 includes a plurality of staple pockets or guides 5053 in a parallel-disposed arrangement along a region 5054 of the anvil 505 that is in opposite correspondence to the first jaw 80. A knife pad 520 is disposed between the plurality of staple guides 5053.

FIG. 8(d) is an exploded view of a side plate component 560. The side plate component 560 has a top plate 5601 and a side plate 5602. The top plate 5601 has a first slot 5603 and a second slot 5604, each of which has a side-disposed open end. Also, the top plate 5601 has a third slot 5605 that has a rear-disposed open end. Mounted, e.g., by welding, to the side plate component 560 is a swivel arm sleeve 570 that has a longitudinally arranged internal bore 5701 extending therethrough. A portion of the bore 5701 is cut away so as to form a vertically disposed slot 5702. An internal surface of the bore 5701 has an opening into which is integrally mounted a part of the camming arrangement, e.g., a cam follower 571 such as a ball bearing.

FIG. 8(e) is a partially-exploded perspective view of the surgical device 11, according to one example embodiment of the present invention. According to this example embodiment, the second jaw 50 includes the anvil component 504. The anvil component 504 is shown in FIG. 8(e) as being assembled, relative to the exploded view illustrated in FIG. 8(c).

The first jaw 80 includes a second side plate component 506. An external surface 5062 of the second side plate component 506 has an arrangement for mounting a gear housing 255. The gear housing 255 is mounted to the external surface 5062 of the second side plate component 506 via fasteners, e.g., screws 533.

A quick-connect coupling 511 is mounted onto the gear housing 255 and is biased via a set of springs. The gear housing 255 includes the first drive socket 180 and the second drive socket 310. In this example embodiment, the first drive socket 180 includes a first pinion 508a (hidden), one end of which extends through an opening 2551 of the gear housing 255 and the other end of which includes spur gear teeth. The second drive socket 310 includes the second pinion 508b (hidden), one end of which extends through a second opening 2552 of the gear housing 255 and the other end of which includes an engagement end. A memory module 501 is arranged in the gear housing 255 and includes a connector that extends through, or is accessible through, an opening of the gear housing 255. The memory module 501 is maintained in position within the gear housing 255 by inboard and outboard shims. The memory module 501 is also biased in its position by a spring 539.

The first and second pinions 508a and 508b engage a spur gear 529a and a coupling element 529b, respectively. The first spur gear 529a includes an internal bore 5293 (shown in dotted line) which non-rotatably engages an end 5231 of the first worm 523a. The coupling element 529b includes an internal bore 5294 which non-rotatably engages an end 5234 of the second worm 523b and which non-rotatably engages the engagement end of the second pinion 508b. As illustrated in FIG. 8(a), the bores 5293 and 5294, the ends 5231, 5234, and the engagement end of the second pinion 508b may be, e.g., square. It should be understood that the bores 5293, 5294, the ends 5231, 5234, and the engagement end of the second pinion 508b may have any shape or configuration that provides non-rotatable engagement therebetween.

In this example embodiment, the first worm 523a has one end 5231, which non-rotatably engages the internal bore 5293 of the first spur gear 529a, and a second end 5232, which includes circumferentially-disposed thread(s) 5233. The second worm 523b has one end 5234, which non-rotatably engages the internal bore 5294 of the coupling element 529b, and a second end 5235 which includes circumferentially-disposed threads 5236. The second end 5232 of the first worm 523a extends through a hole 5607 in the side plate 5602 of the side plate component 560, and the end 5231 of the worm 523a engages the first spur gear 529a. The second end 5235 of the second worm 523b extends through a hole 5606 in the side plate 5602 of the side plate component 560, and the end 5234 of the worm 523b engages the coupling element 529b.

Also disposed within the surgical device 11 is a worm gear 522. The worm gear 522 has circumferentially-disposed teeth 5221, which engage the thread(s) 5233 of the second end 5232 of the worm 523a. The worm gear 522 includes an internal bore through which is disposed a screw 521. The screw 521 has a head 5211 under which is formed a circumferential groove 5222. The screw 521 non-rotatably engages the internal bore of worm gear 522. The worm gear 522 and the screw 521 may be separately or integrally formed. The head 5211 and the groove 5222 are configured to fit and be retained within the slot 5605 of the side plate component 560. The screw 521 has externally-disposed threads 5214, which engage the internally-threaded bore 5051 of the swivel arm 509.

A worm gear 516 and a worm gear 517 are also disposed within the surgical device 11. The worm gear 516 and the worm gear 517 are positioned on opposite sides of the worm 523*b*. Specifically, the worm gear 516 includes circumferentially-disposed gear teeth 5161, which engage a first side of the worm 523*b*, and the worm gear 517 includes circumferentially-disposed gear teeth 5171, which engage a second side of the worm 523*b*. The worm gear 516 includes a head 5162, under which is formed a circumferential groove 5163. The head 5162 and the groove 5163 are configured to fit and be maintained within the slot 5606 of the side plate component 560, so that the worm gear 516 is rotatable about its vertical central axis. The worm gear 517 includes a head 5172, under which is formed a circumferential groove 5173. The head 5172 and the groove 5173 are configured to fit and be maintained within the slot 5607 of the side plate component 560, so that the worm gear 517 is rotatable about its vertical central axis.

The externally-threaded screw 504 of the thrust plate assembly 5031 (shown in FIG. 8(*e*) as being assembled, relative to the exploded view illustrated in FIG. 8(*b*)) is disposed through an internally-threaded bore 5164 of the worm gear 516. The externally-threaded screw 503 is disposed through an internally-threaded bore 5174 of the worm gear 517. Because the worm gears 516 and 517 are located on, and engage, opposite sides of the worm 523*b*, the internally-threaded bores 5164 and 5174 of the worm gears 516 and 517, as well as the externally-threaded screws 504 and 503, may be oppositely threaded relative to each other. In the example embodiment illustrated, the internally-threaded bore 5164 of the worm gear 516 may have a right-hand thread, which engages the right-hand external thread of the screw 504, and the internally-threaded bore 5174 of the worm gear 517 may have a left-handed thread, which engages the left-handed external thread of the screw 503. As set forth above, both the screws 503 and 504 are fixedly coupled to the top surface 5021 of the thrust plate 502.

The staple cartridge assembly 507, shown assembled in FIG. 8(*e*) relative to the exploded view illustrated in FIG. 8(*a*), is arranged such that the staple pusher 514 is positioned below the bottom surface 5022 of the thrust plate 502. The staple holder 513 is disposed below the staple pusher 514.

To assemble the surgical device 11, the proximal end 5071 of the staple cartridge assembly 507 is mated with surfaces 5073 on the sides of the slot 5702 of the swivel arm sleeve 570. The gears are arranged between the thrust plate component 5031 and the top plate 5601 of the side plate component 560 and are maintained in position in part by their engagement with the slots and openings of the side plate components 560, e.g., by the engagement of the heads, e.g., head 5162, 5172 and 5211, within the slots, e.g., slots 5603, 5604 and 5605, of the side plate component 560. The threads 5214 of the screw 521 are engaged with the internally-threaded bore 5051 of the swivel arm 509. The swivel arm 509 resides within the central bore 5701 of the swivel arm sleeve 570. The cam follower 571 is maintained within and extends internally within the bore 5071 of the swivel arm sleeve such that a portion of the cam follower 571 is within the channel 5052 of the swivel arm 509.

The second side plate component 506 is attached, e.g., by screws 599, to the side plate component 560 such that the gears, the thrust plate component 5031, the staple cartridge assembly 507 and the swivel arm 509 (within the swivel arm sleeve 570) are disposed therebetween. The gear housing 255 is attached to the second side plate component 506, e.g., by screws 533.

FIG. 9 is a perspective view of the fully-assembled surgical device 11 in the open position. It should be understood that while the example embodiments of the present invention illustrated in FIGS. 3 to 9 include a guillotine-type arrangement of the stapling and cutting elements, in another embodiment, a stapling and cutting element is moved between a proximal end and a distal end of the surgical device 11. For example, an alternative example embodiment of the surgical device 11 may include gears coupled to a stapling and cutting element that is moved between a proximal end and a distal end of the surgical device 11, the gears driven by drive shafts that are coupled in non-parallel, e.g., perpendicular, correspondence to the plane of movement of the first jaw 80 and the second jaw 50.

Furthermore, it should be understood that while the example embodiments of the present invention illustrated in FIGS. 3 to 9 include an arrangement in which the drive sockets 180, 310 are configured to engage drive shafts, e.g., drive shafts 630 and 632, respectively, that are rotatable about a rotation axis arranged in non-parallel, e.g., perpendicular, correspondence to the x-y plane (see, for instance, FIG. 3), in another embodiment, the surgical device 11 may provide an arrangement in which the drive sockets 180, 310 are configured to engage drive shafts, e.g., drive shafts 630 and 632, respectively, that are rotatable about a rotation axis arranged in parallel correspondence to the x-y plane.

Still further, it should be understood that the caroming arrangement for swiveling the second jaw 50 relative to the first jaw 80 may have various different configurations. For instance, the channel 5052 that is shown and described as being on the swivel arm 509 may be disposed on one or both of the swivel arm and the swivel arm sleeve 570. Furthermore, the channel 5052 of the swivel arm 509 may have a different shape than the shape described hereinabove. Rather, the present invention may include any caroming arrangement configured to move the second jaw 50 into non-parallel correspondence relative to the plane defined by the first and second jaws when in the closed position.

Still further, it should be understood that while the example embodiments of the present invention illustrated in FIGS. 3 to 9 include an arrangement in which the clamping surfaces of the first and second jaws define planes that remain in parallel correspondence relative to each other during operation, in another embodiment, the surgical device 11 may provide an arrangement in which the clamping surfaces of the first and second jaws define planes that do not remain in parallel correspondence relative to each other during operation. For example, in an example embodiment, the surgical device 11 may provide an arrangement in which the first and second jaws open and close at least partially in a scissor-type fashion, the first and second jaws being connected at their respective proximal ends by, e.g., a hinge, etc. For instance, the surgical device may provide an arrangement whereby the second jaw is coupled to and is moveable relative to the first jaw between a closed position and an intermediate open position wherein, between the closed position and the intermediate open position, the clamping surfaces of the first and second jaws define first and second planes that remain in parallel correspondence relative to each other. In addition, the second jaw may be further moveable relative to the first jaw between the intermediate open position and a fully opened position wherein, between the intermediate open position and the fully opened position, the first and second planes defined by the clamping surfaces of the first and second jaws are moved out of parallel correspondence relative to each other, e.g., the first and second jaws move in a scissor-like fashion between the intermediate open position and the fully open position. Such an arrangement is illustrated, for example, in FIGS. 20(*a*)-(*c*), which are various views of a cutting and stapling attachment according to another example embodiment of the present invention. Specifically, FIG. 20(*a*) is a perspective view of a device having such an arrangement. FIG. 20(*b*) is a cross-sectional view of this device taken through a lead screw. FIG. 20(*c*) is a cross-sectional view of this device taken through a cam pin.

Still further, it should be understood that while the example embodiments of the present invention illustrated in FIGS. 3 to 9 include an arrangement in which the first and second jaws move at least rotationally relative to each other during a portion of the operation such that the second jaw is caused to move out of a plane defined by the first and second jaws when the first and second jaws are in the fully closed position, in an example embodiment, the surgical device 11 may provide an arrangement in which the first and second jaws do not move at least rotationally relative to each other out of a plane defined by the first and second jaws when the first and second jaws are in the fully closed position. For example, in an example embodiment, the surgical device 11 may provide an arrangement in which the first and second jaws open and close at least partially in a scissor-type fashion, the first and second jaws being connected at their respective proximal ends by, e.g., a hinge, etc., such that the second jaw is maintained in the plane defined by the first and second jaws when the first and second jaws are in the fully closed position. For instance, the surgical device may provide an arrangement whereby the second jaw is coupled to and is moveable relative to the first jaw between a closed position and an intermediate open position wherein, between the closed position and the intermediate open position, the first and second jaws are maintained within a plane defined by the first and second jaws when the first and second jaws are in the fully closed position. In addition, the second jaw may be further moveable relative to the first jaw between the intermediate open position and a fully opened position wherein, between the intermediate open position and the fully opened position, the first and second jaws are moved in a scissor-like fashion while being maintained within the plane defined by the first and second jaws when the first and second jaws are in the fully closed position.

According to one example embodiment of the present invention, the surgical device 11 may be configured as an attachment to, or may be integral with, an electro-mechanical surgical system, such as electro-mechanical driver component 610. In another example embodiment, the surgical device may be an attachment to, or may integral with, a mechanical driver system.

FIG. 2 is a perspective view of an example embodiment of an electro-mechanical driver component 610 according to the present invention. Examples of such an electro-mechanical driver component are described in, e.g., U.S. patent application Ser. No. 09/723,715, U.S. patent application Ser. No. 09/836,781 and U.S. patent application Ser. No. 09/887,789, each of which is expressly incorporated herein in their entirety by reference thereto. The electro-mechanical driver component 610 may include, for example, a remote power console 612, which includes a housing 614 having a front panel 615. Mounted on the front panel 615 are a display device 616 and indicators 618*a*, 618*b*. A flexible shaft 620 may extend from the housing 614 and may be detachably attached thereto via a first coupling 622. The distal end 624 of the flexible shaft 620 may include a second coupling 626 adapted to detachably attach, e.g., the surgical device 11 described above, to the distal end 624 of the flexible shaft 620. The second coupling 626 may also be adapted to detachably attach a different surgical instrument or attachment. In another example embodiment, the distal end 624 of the flexible shaft 620 may permanently attach to or be integral with a surgical instrument.

Figure 10:
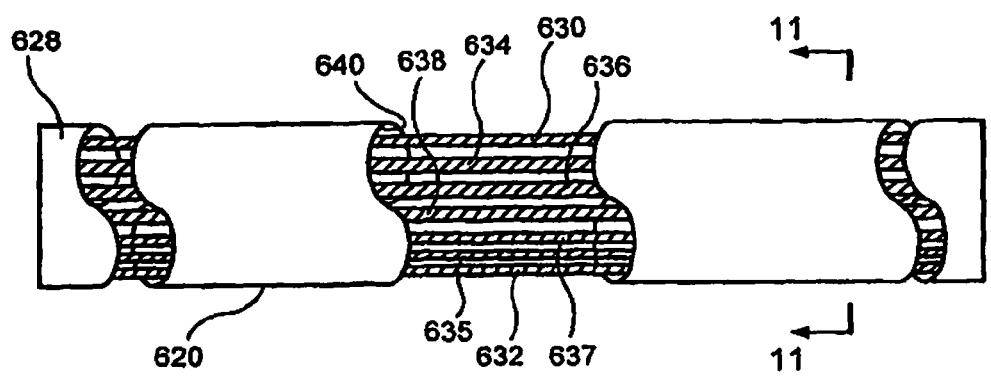
FIG. 10 is a side elevational view, partially in section, of a flexible shaft of the electro-mechanical surgical device illustrated in FIG. 2.
Figure 11:
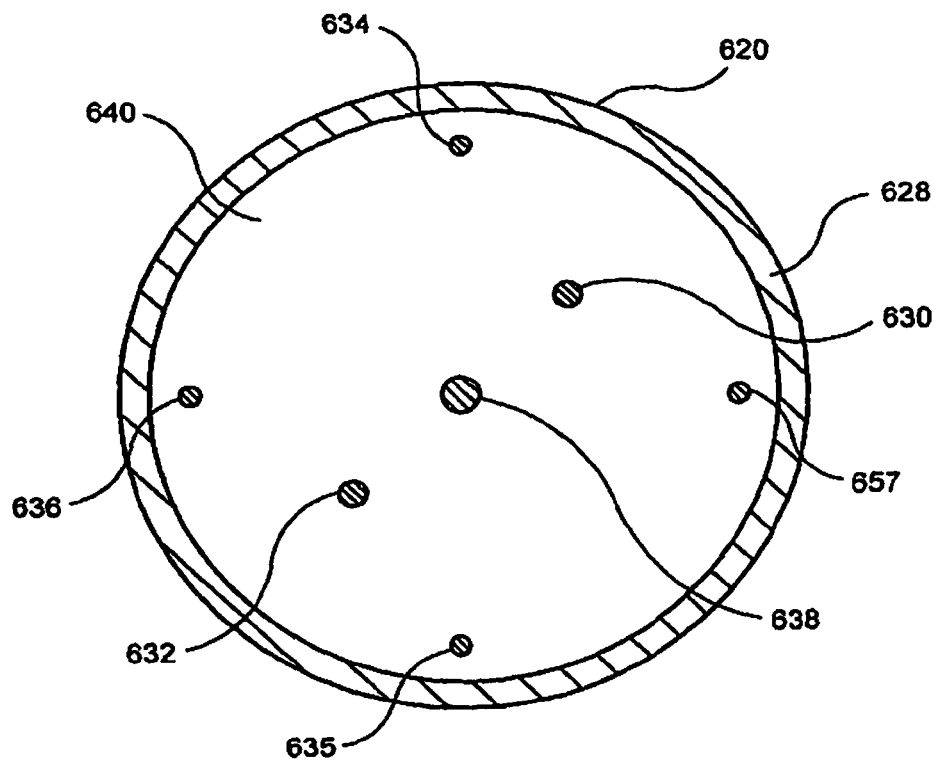
FIG. 11 is a cross-sectional view of the flexible shaft taken along the line 11-11 shown in FIG. 10.

Referring to FIG. 10, there is seen a side view, partially in section, of flexible shaft 620. According to one example embodiment, the flexible shaft 620 includes a tubular sheath 628, which may include a coating or other sealing arrangement configured to provide a fluid-tight seal between the interior channel 640 thereof and the environment. The sheath 628 may be formed of a tissue-compatible, sterilizable elastomeric material. The sheath 628 may also be formed of a material that is autoclavable. Disposed within the interior channel 640 of the flexible shaft 620, and extending along the entire length thereof, may be a first rotatable drive shaft 630, a second rotatable drive shaft 632, a first steering cable 634, a second steering cable 635, a third steering cable 636, a fourth steering cable 637 and a data transfer cable 638. FIG. 11 is a cross-sectional view of the flexible shaft 620 taken along the line 11-11 illustrated in FIG. 10 and further illustrates the several cables 630, 632, 634, 635, 636, 637, 638. Each distal end of the steering cables 634, 635, 636, 637 is affixed to the distal end 624 of the flexible shaft 620. Each of the several cables 630, 632, 634, 635, 636, 637, 638 may be contained within a respective sheath.

The first rotatable drive shaft 630 and the second rotatable drive shaft 632 may be configured, for example, as highly flexible drive shafts, such as, for example, braided or helical drive cables. It should be understood that such highly flexible drive cables may have limited torque transmission characteristics and capabilities. It should also be understood that the surgical device 11, or other attachments connected to the flexible shaft 620, may require a higher torque input than the torque transmittable by the drive shafts 630, 632. The drive shafts 630, 632 may thus be configured to transmit low torque but high speed, the high-speed/low-torque being converted to low-speed/high-torque by gearing arrangements disposed, for example, at the distal end and/or the proximal end of the flexible shaft 620, in the surgical instrument or attachment and/or in the remote power console 612. It should be appreciated that such gearing arrangement(s) may be provided at any suitable location along the power train between the motors disposed in the housing 614 and the attached surgical instrument or other attachment connected to the flexible shaft 620. Such gearing arrangement(s) may include, for example, a spur gear arrangement, a planetary gear arrangement, a harmonic gear arrangement, cycloidal drive arrangement, an epicyclic gear arrangement, etc.

Figure 12:
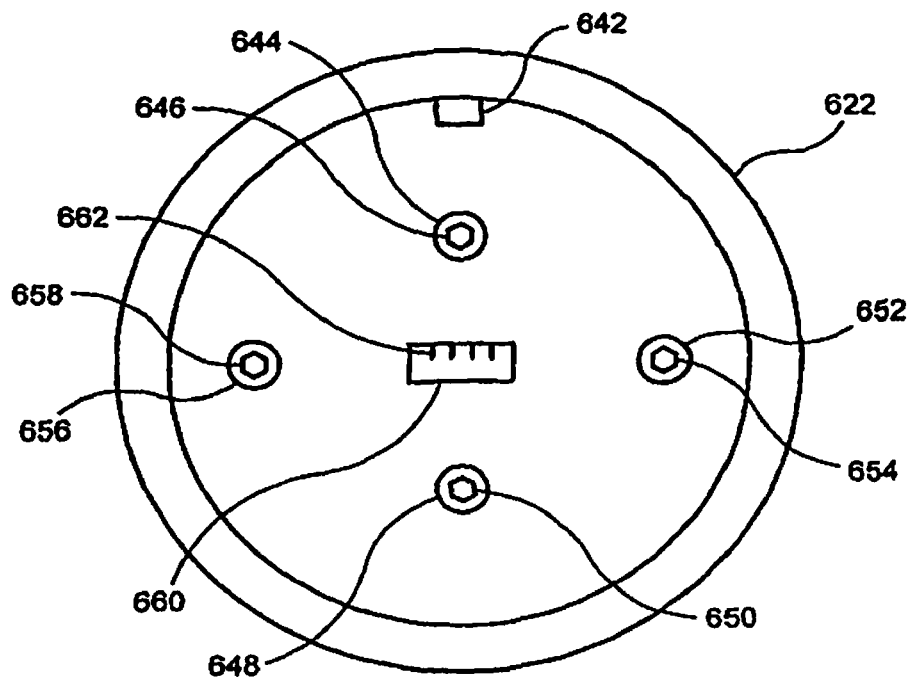
FIG. 12 is a rear end view of a first coupling of the flexible shaft illustrated in FIG. 10.

Referring now to FIG. 12, there is seen a rear end view of the first coupling 622. The first coupling 622 includes a first connector 644, a second connector 648, a third connector 652 and a fourth connector 656, each rotatably secured to first coupling 622. Each of the connectors 644, 648, 652, 656 includes a respective recess 646, 650, 654, 658. As illustrated in FIG. 12, each recess 646, 650, 654, 658 may be hexagonally shaped. It should be appreciated, however, that the recesses 646, 650, 654, 658 may have any shape and configuration adapted to non-rotatably couple and rigidly attach the connectors 644, 648, 652, 656 to respective drive shafts of the motor arrangement contained within the housing 612. It should be appreciated that complementary projections may be provided on respective drive shafts of the motor arrangement to thereby drive the drive elements of the flexible shaft 620. It should also be appreciated that the recesses may be provided on the drive shafts and complementary projections may be provided on the connectors 644, 648, 652, 656. Any other coupling arrangement configured to non-rotatably and releasably couple the connectors 644, 648, 652, 656 and the drive shafts of the motor arrangement may be provided.

One of the connectors 644, 648, 652, 656 is non-rotatably secured to the first drive shaft 630, and another one of the connectors 644, 648, 652, 656 is non-rotatably secured to the second drive shaft 632. The remaining two of the connectors 644, 648, 652, 656 engage with transmission elements configured to apply tensile forces on the steering cables 634, 635, 636, 637 to thereby steer the distal end 624 of the flexible shaft 620. The data transfer cable 638 is electrically and logically connected with a data connector 660. The data connector 660 includes, for example, electrical contacts 662, corresponding to and equal in number to the number of individual wires contained in the data cable 638. The first coupling 622 includes a key structure 642 configured to properly orient the first coupling 622 to a mating and complementary coupling arrangement disposed on the housing 612. Such key structure 642 may be provided on either one, or both, of the first coupling 622 and the mating and complementary coupling arrangement disposed on the housing 612. The first coupling 622 may include a quick-connect type connector, which may engage the first coupling 622 to the housing 612 by a simple pushing motion. Seals may be provided in conjunction with any of the several connectors 644, 648, 652, 656, 660 to provide a fluid-tight seal between the interior of the first coupling 622 and the environment.

Figure 13:
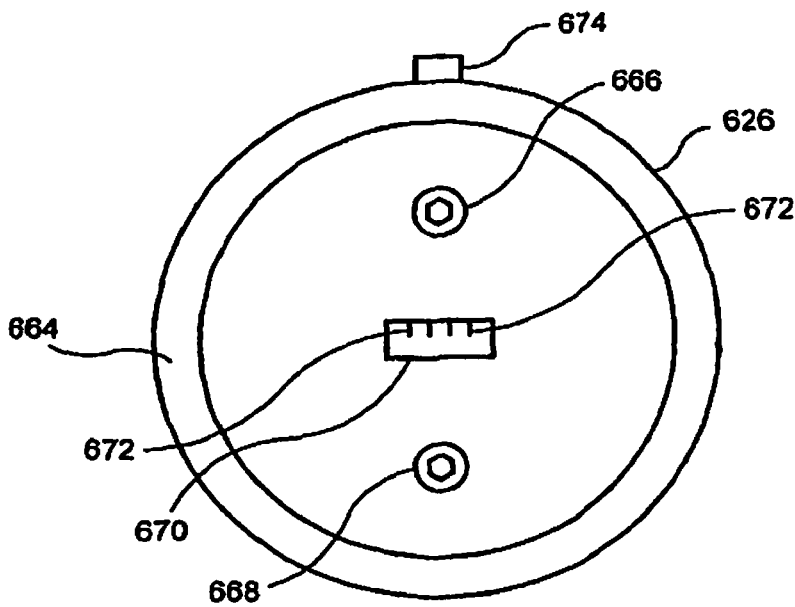
FIG. 13 is a front end view of a second coupling of the flexible shaft illustrated in FIG. 10.

Referring now to FIG. 13, there is seen a front end view of the second coupling 626 of the flexible shaft 620. In the example embodiment, the second coupling 626 includes a first connector 666 and a second connector 668, each rotatably secured to the second coupling 626 and each non-rotatably secured to a distal end of a respective one of the first and second drive shafts 630, 632. A quick-connect type fitting 664 is provided on the second coupling 626 to detachably secure the surgical device 11 thereto. The quick-connect type fitting 664 may be, for example, a rotary quick-connect type fitting, a bayonet type fitting, etc. A key structure 674 is provided on the second coupling 626 and configured to properly align the surgical device 11 to the second coupling 626. The key structure or other arrangement configured to properly align the surgical device 11 to the flexible shaft 620 may be provided on either one, or both, of the second coupling 626 and the surgical device 11. In addition, the quick-connect type fitting may be provided on the surgical device 11, as illustrated in FIG. 8(*e*) as the quick connect coupling 511. A data connector 670 having electrical contacts 672 is also provided in the second coupling 626. Like the data connector 660 of the first coupling 622, the data connector 670 of the second coupling 626 includes contacts 672 electrically and logically connected to the respective wires of the data transfer cable 638 and contacts 662 of the data connector 660. Seals may be provided in conjunction with the connectors 666, 668, 670 to provide a fluid-tight seal between the interior of the second coupling 626 and the environment.

Disposed within the housing 614 of the remote power console 612 are electro-mechanical driver elements configured to drive the drive shafts 630, 632 and the steering cables 634, 635, 636, 637 to thereby operate the electro-mechanical driver component 610 and the surgical device 11 attached to the second coupling 626. In the example embodiment illustrated schematically in FIG. 14, five electric motors 676, 680, 684, 690, 696, each operated via a power source, may be disposed in the remote power console 612. It should be appreciated, however, that any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors.

Figure 14:
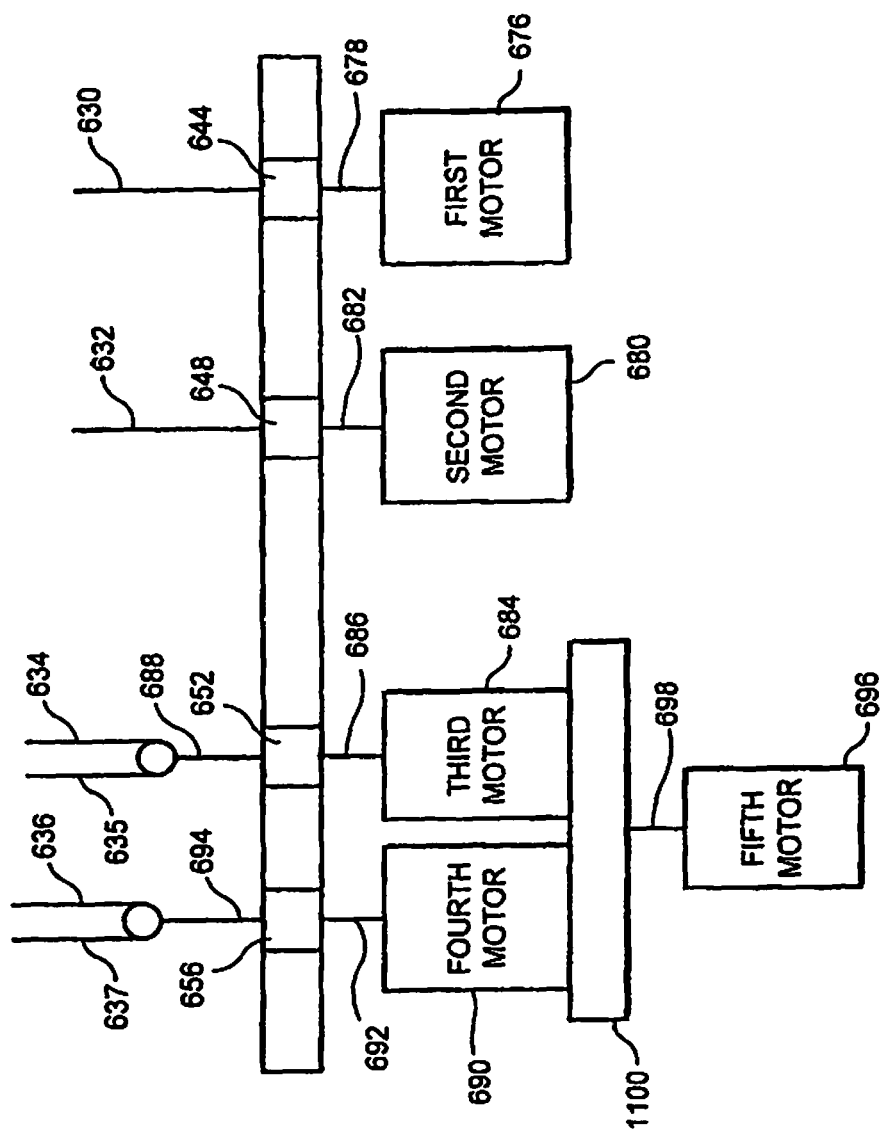
FIG. 14 is a schematic view of a motor arrangement of the electro-mechanical surgical system illustrated in FIG. 2.

FIG. 14 illustrates schematically one possible arrangement of motors. An output shaft 678 of a first motor 676 engages with the first connector 644 of the first coupling 622 when the first coupling 622, and, therefore, the flexible shaft 620, is engaged with the housing 614 to thereby drive the first drive shaft 630 and the first connector 666 of the second coupling 626. Similarly, an output shaft 682 of a second motor 680 engages the second connector 648 of the first coupling 622 when the first coupling 622, and, therefore, the flexible shaft 620 is engaged with the housing 614 to thereby drive the second drive shaft 632 and the second connector 668 of the second coupling 626. An output shaft 686 of a third motor 684 engages the third connector 652 of the first coupling 622 when the first coupling 622, and, therefore, the flexible shaft 620, is engaged with the housing 614 to thereby drive the first and second steering cables 634, 635 via a first pulley arrangement 688. An output shaft 692 of a fourth motor 690 engages the fourth connector 656 of the first coupling 622 when the first coupling 622, and, therefore, the flexible shaft 620, is engaged with the housing 614 to thereby drive the third and fourth steering cables 636, 637 via a second pulley arrangement 694. The third and fourth motors 684, 690 may be secured on a carriage 1100, which is selectively movable via an output shaft 698 of a fifth motor 696 between a first position and a second position to selectively engage and disengage the third and fourth motors 684, 690 with the respective pulley arrangement 688, 694 to thereby permit the flexible shaft 620 to become taut and steerable or limp as necessary. It should be appreciated that other mechanical, electrical and/or electro-mechanical mechanisms, etc., may be used to selectively engage and disengage the steering mechanism. The motors may be arranged and configured as described, for example, in U.S. patent application Ser. No. 09/510,923, entitled A Carriage Assembly for Controlling a Steering Wire Mechanism Within a Flexible Shaft" which was filed on Feb. 22, 2000, now issued as U.S. Pat. No. 6,517,565 on Feb. 11, 2003, which is expressly incorporated herein in its entirety by reference thereto.

It should be appreciated that any one or more of the motors 676, 680, 684, 690, 696 may be, for example, a high-speed/low-torque motor, a low-speed/high-torque motor, etc. As indicated above, the first rotatable drive shaft 630 and the second rotatable drive shaft 632 may be configured to transmit high speed and low torque. Thus, the first motor 676 and the second motor 680 may be configured as high-speed/low-torque motors. Alternatively, the first motor 676 and the second motor 680 may be configured as low-speed/high-torque motors with a torque-reducing/speed-increasing gear arrangement disposed between the first motor 676 and the second motor 680 and a respective one of the first rotatable drive shaft 630 and the second rotatable drive shaft 632. Such torque-reducing/speed-increasing gear arrangements may include, for example, a spur gear arrangement, a planetary gear arrangement, a harmonic gear arrangement, cycloidal drive arrangement, an epicyclic gear arrangement, etc. It should be appreciated that any such gear arrangement may be disposed within the remote power console 612 or in the proximal end of the flexible shaft 620, such as, for example, in the first coupling 622. It should be appreciated that the gear arrangement(s) may be provided at the distal and/or proximal ends of the first rotatable drive shaft 630 and/or the second rotatable drive shaft 632 to prevent windup and breakage thereof.

Figure 15:
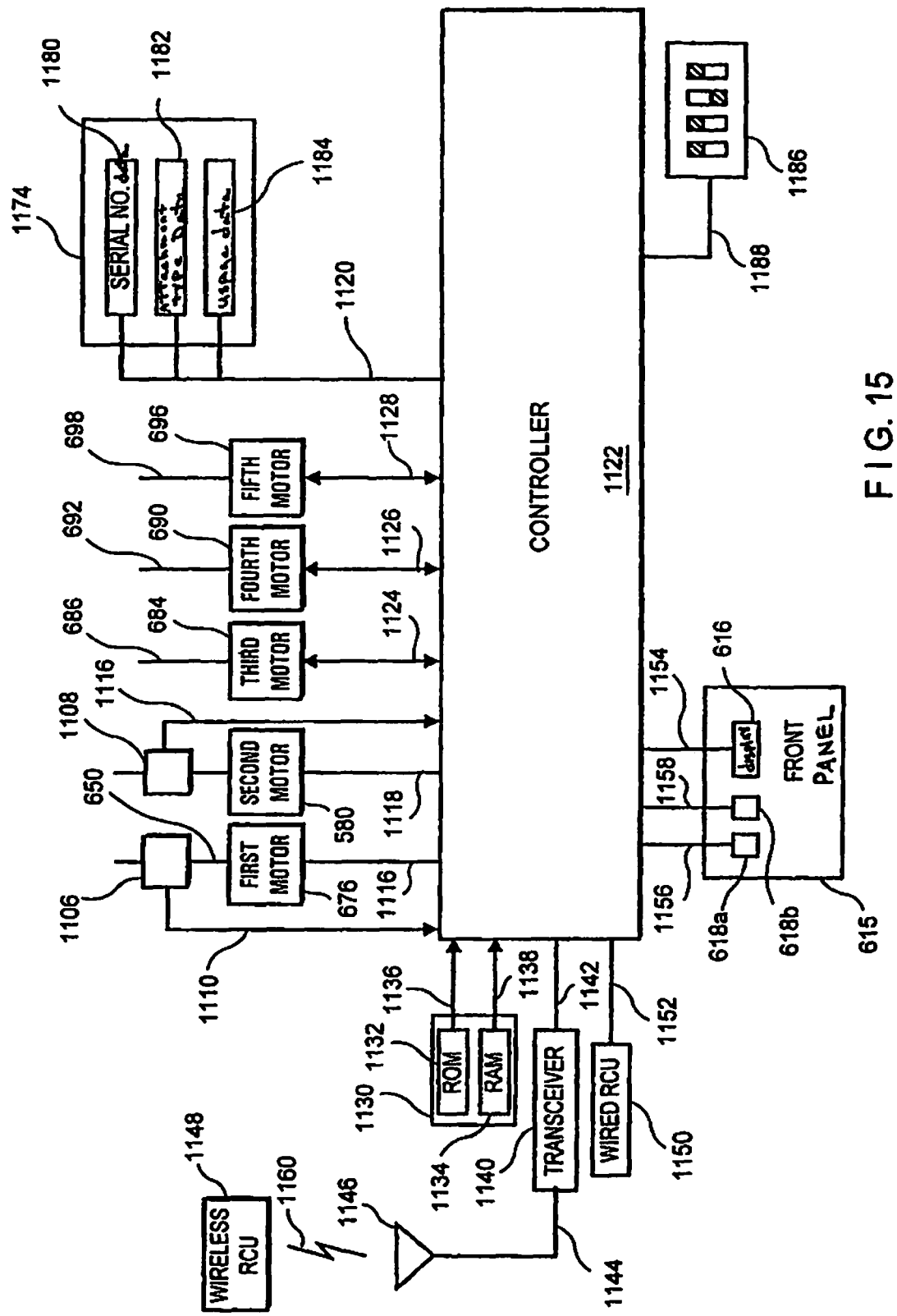
FIG. 15 is a schematic view of the electro-mechanical surgical system illustrated in FIG. 2.

Referring now to FIG. 15, there is seen a schematic view of the electro-mechanical driver component 610. A controller 1122 is provided in the housing 614 of the remote power console 612 and is configured to control all functions and operations of the electro-mechanical driver component 610 and the linear clamping, cutting and stapling device 11 or other surgical instrument or attachment attached to the flexible shaft 620. A memory unit 1130 is provided and may include memory devices, such as, a ROM component 1132, a RAM component 1134, etc. The ROM component 1132 is in electrical and logical communication with the controller 1122 via a line 1136, and the RAM component 1134 is in electrical and logical communication with the controller 1122 via a line 1138. The RAM component 1134 may include any type of random-access memory, such as, for example, a magnetic memory device, an optical memory device, a magneto-optical memory device, an electronic memory device, etc. Similarly, the ROM component 1132 may include any type of read-only memory, such as, for example, a removable memory device, such as a PC-Card or PCMCIA-type device. It should be appreciated that the ROM component 1132 and the RAM component 1134 may be configured as a single unit or may be separate units and that the ROM component 1132 and/or the RAM component 1134 may be provided in the form of a PC-Card or PCMCIA-type device.

The controller 1122 is further connected to the front panel 615 of the housing 614 and, more particularly, to the display device 616 via a line 1154 and indicators 618a, 618b via respective lines 1156, 1158. The lines 1116, 1118, 1124, 1126, 1128 electrically and logically connect the controller 1122 to the first, second, third, fourth and fifth motors 676, 680, 684, 690, 696, respectively. A wired remote control unit ("RCU") 1150 is electrically and logically connected to the controller 1122 via a line 1152. A wireless RCU 1148 is also provided and communicates via a wireless link 1160 with a receiving/sending unit 1146 connected via a line 1144 to a transceiver 1140. The transceiver 1140 is electrically and logically connected to the controller 1122 via a line 1142. The wireless link 1160 may be, for example, an optical link, such as an infrared link, a radio link or any other form of wireless communication link.

A switch device 1186, which may include, for example, an array of DIP switches, may be connected to the controller 1122 via a line 1188. The switch device 1186 may be configured, for example, to select one of a plurality of languages used in displaying messages and prompts on the display device 616. The messages and prompts may relate to, for example, the operation and/or the status of the electro-mechanical driver component 610 and/or to the surgical device 11 attached thereto.

According to the example embodiment of the present invention, a first encoder 1106 is provided within the second coupling 626 and is configured to output a signal in response to and in accordance with the rotation of the first drive shaft 630. A second encoder 1108 is also provided within the second coupling 626 and is configured to output a signal in response to and in accordance with the rotation of the second drive shaft 632. The signal output by each of the encoders 1106, 1108 may represent the rotational position of the respective drive shaft 630, 632 as well as the rotational direction thereof. Such encoders 1106, 1108 may include, for example, Hall-effect devices, optical devices, etc. Although the encoders 1106, 1108 are described as being disposed within the second coupling 626, it should be appreciated that the encoders 1106, 1108 may be provided at any location between the motor system and the surgical device 11. It should be appreciated that providing the encoders 1106, 1108 within the second coupling 626 or at the distal end of the flexible shaft 620 may provide an accurate determination of the drive shaft rotation. If the encoders 1106, 1108 are disposed at the proximal end of the flexible shaft 620, windup of the first and second rotatable drive shafts 630, 632 may result in measurement error.

Figure 16:
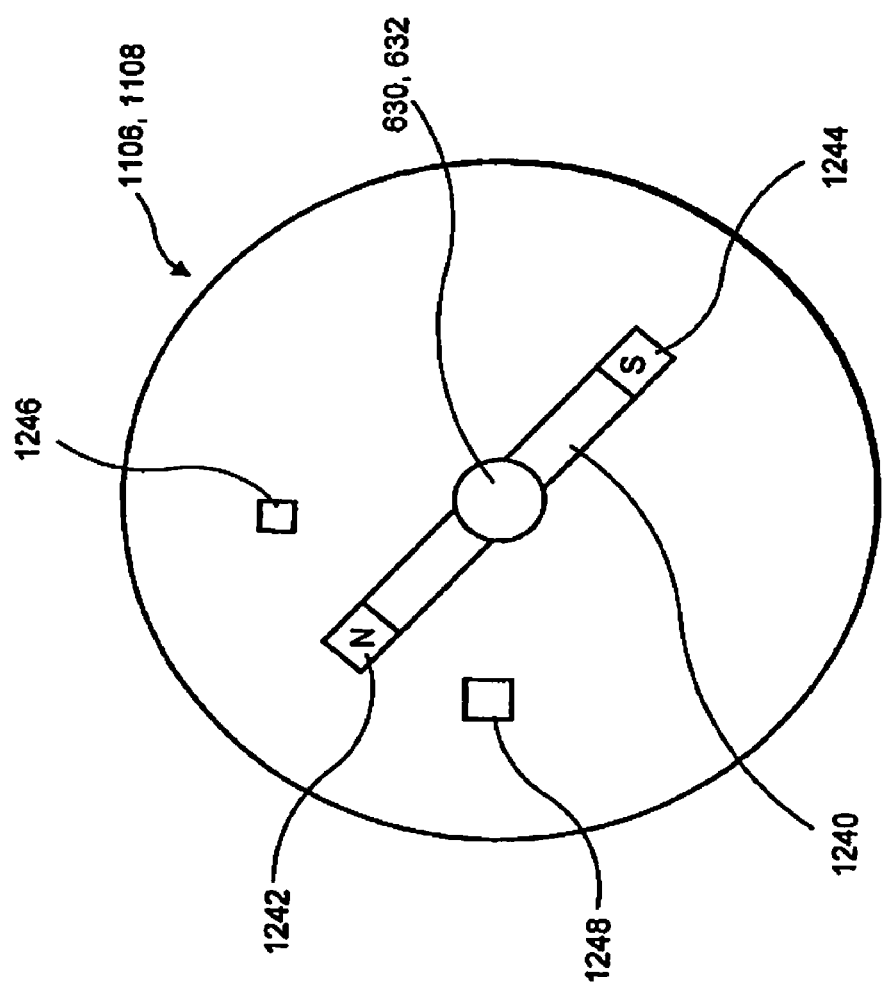
FIG. 16 is a schematic view of an encoder of the flexible shaft illustrated in FIG. 10.

FIG. 16 is a schematic view of an encoder 1106, 1108, which includes a Hall-effect device. Mounted non-rotatably on the drive shafts 630, 632 is a magnet 1240 having a north pole 1242 and a south pole 1244. The encoder 1106, 1108 further includes a first sensor 1246 and a second sensor 1248, which are disposed approximately 90° apart relative to the longitudinal, or rotational, axis of the drive shafts 630, 632. The output of the sensors 1246, 1248 is persistent and changes its state as a function of a change of polarity of the magnetic field in the detection range of the sensor. Thus, based on the output signal from the encoders 1106, 1108, the angular position of the drive shaft 630, 632 may be determined within one-quarter revolution and the direction of rotation of the drive shaft 630, 632 may be determined. The output of each encoder 1106, 1108 is transmitted via a respective line 1110, 1112 of the data transfer cable 638 to the controller 1122. The controller 1122, by tracking the angular position and rotational direction of the drive shafts 630, 632 based on the output signal from the encoders 1106, 1108, may thereby determine the position and/or state of the components of the surgical device connected to the electro-mechanical driver component 610. That is, by counting the revolutions of the drive shaft 630, 632, the controller 1122 may determine the position and/or state of the components of the surgical device connected to the electro-mechanical driver component 610.

For example, the advancement distance between the first jaw 80 and the second jaw 50 and the thrust plate 502 are functions of, and ascertainable on the basis of, the rotation of the respective drive shafts 630, 632. By ascertaining an absolute position of the second jaw 50 and the thrust plate 502 at a point in time, the relative displacement of the second jaw 50 and the thrust plate 502, based on the output signal from the encoders 1106, 1108 and the known pitches of the screw 521 and of the screws 503 and 504, may be used to ascertain the absolute position of the first jaw 80 and the thrust plate 502 at all times thereafter. The absolute position of the second jaw 50 and the thrust plate 502 may be fixed and ascertained at the time that the surgical device 11 is first coupled to the flexible shaft 620. Alternatively, the position of the second jaw 50 and the thrust plate 502 relative to, for example, the first jaw 80 may be determined based on the output signal from the encoders 1106, 1108.

The surgical device 11 may further include, as illustrated in FIG. 8(e), a data connector 1272 adapted by size and configuration to electrically and logically connect to the connector 670 of the second coupling 626. In the example embodiment, the data connector 1272 includes contacts equal in number to the number of leads 672 of the connector 670. The memory module 501 is electrically and logically connected with the data connector 1272. The memory module 501 may be in the form of, for example, an EEPROM, EPROM, etc. and may be contained, for example, within the second jaw 50 of the surgical device 11.

Figure 17:
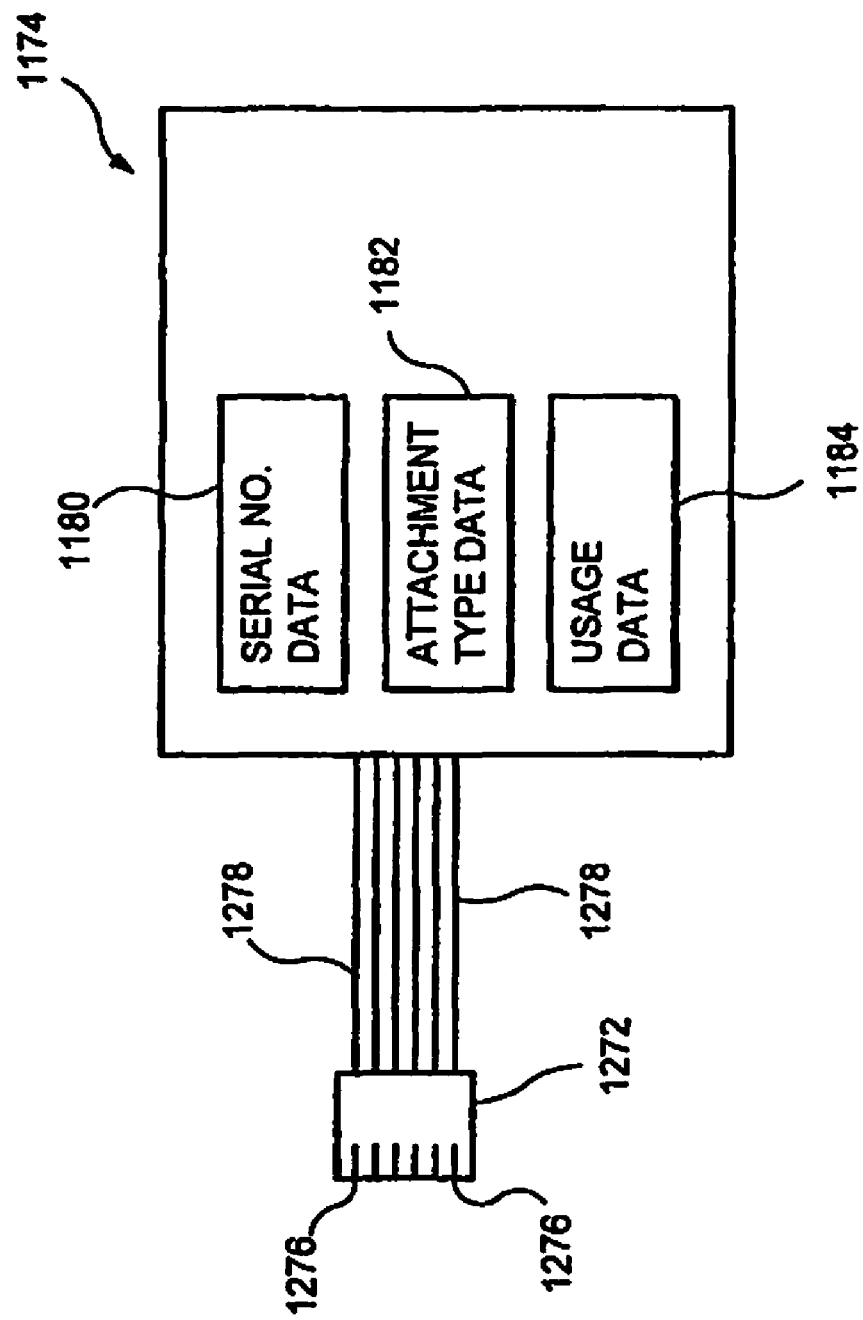
FIG. 17 is a schematic view of a memory device of a linear clamping, cutting and stapling device according to one example embodiment of the present invention.

FIG. 17 schematically illustrates the memory module 501. As seen in FIG. 17, the data connector 1272 includes the contacts 1276, each electrically and logically connected to the memory module 501 via a respective line 1278. The memory module 501 may be configured to store, for example, a serial number data 1180, an attachment type identifier (ID) data 1182 and a usage data 1184. The memory module 501 may additionally store other data. Both the serial number data 1180 and the ID data 1182 may be configured as read-only data. The serial number data 1180 and/or the ID data 1182 may be stored in a read-only section of the memory module 501. In the example embodiment, the serial number data 1180 may be data uniquely identifying the particular surgical device, whereas the ID data 1182 may be data identifying the type of the attachment, such as, for example, in a system 610 in which other types of surgical instruments or attachments are attachable thereto. The usage data 1184 represents usage of the particular attachment, such as, for example, the number of times the first jaw 80 of the surgical device 11 has been opened and closed, or the number of times that the thrust plate of the surgical device 11 has been advanced. The usage data 1184 may be stored in a read/write section of the memory module 501.

It should be appreciated that the attachment attachable to the distal end 624 of the flexible shaft 620, e.g., the surgical device 11, may be designed and configured to be used a single time or multiple times. The attachment may also be designed and configured to be used a predetermined number of times. Accordingly, the usage data 1184 may be used to determine whether the surgical device 11 has been used and whether the number of uses has exceeded the maximum number of permitted uses. As more fully described below, an attempt to use the attachment after the maximum number of permitted uses has been reached will generate an ERROR condition.

Referring again to FIG. 15, the controller 1122 is configured to read the ID data 1182 from the memory module 501 of the surgical device 11 when the surgical device 11 is initially connected to the flexible shaft 620. The memory module 501 is electrically and logically connected to the controller 1122 via the line 1120 of the data transfer cable 638. Based on the read ID data 1182, the controller 1122 is configured to read or select from the memory unit 1130, an operating program or algorithm corresponding to the type of surgical instrument or attachment connected to the flexible shaft 620. The memory unit 1130 is configured to store the operating programs or algorithms for each available type of surgical instrument or attachment, the controller 1122 selecting and/or reading the operating program or algorithm from the memory unit 1130 in accordance with the ID data 1182 read from the memory module 501 of an attached surgical instrument or attachment. As indicated above, the memory unit 1130 may include a removable ROM component 1132 and/or RAM component 1134. Thus, the operating programs or algorithms stored in the memory unit 1130 may be updated, added, deleted, improved or otherwise revised as necessary. The operating programs or algorithms stored in the memory unit 1130 may be customizable based on, for example, specialized needs of the user. A data entry device, such as, for example, a keyboard, a mouse, a pointing device, a touch screen, etc., may be connected to the memory unit 1130 via, for example, a data connector port, to facilitate the customization of the operating programs or algorithms. Alternatively or additionally, the operating programs or algorithms may be customized and preprogrammed into the memory unit 1130 remotely from the electro-mechanical driver component 610. It should be appreciated that the serial number data 1180 and/or usage data 1184 may also be used to determine which of a plurality of operating programs or algorithms is read or selected from the memory unit 1130. It should be appreciated that the operating program or algorithm may alternatively be stored in the memory module 501 of the surgical device 11 and transferred to the controller 1122 via the data transfer cable 638. Once the appropriate operating program or algorithm is read by or selected by or transmitted to, the controller 1122, the controller 1122 causes the operating program or algorithm to be executed in accordance with operations performed by the user via the wired RCU 1150 and/or the wireless RCU 1148. As indicated hereinabove, the controller 1122 is electrically and logically connected with the first, second, third, fourth and fifth motors 676, 680, 684, 690, 696 via respective lines 1116, 1118, 1124, 1126, 1128 and is configured to control such motors 676, 680, 684, 690, 696 in accordance with the read, selected or transmitted operating program or algorithm via the respective lines 1116, 1118, 1124, 1126, 1128. It should also be recognized that the above-described features and operation with respect to the memory unit 501 may also be applicable to memory unit 5011, e.g., see for instance FIG. 8(*a*), corresponding to the staple cartridge assembly 507.

Figure 18:
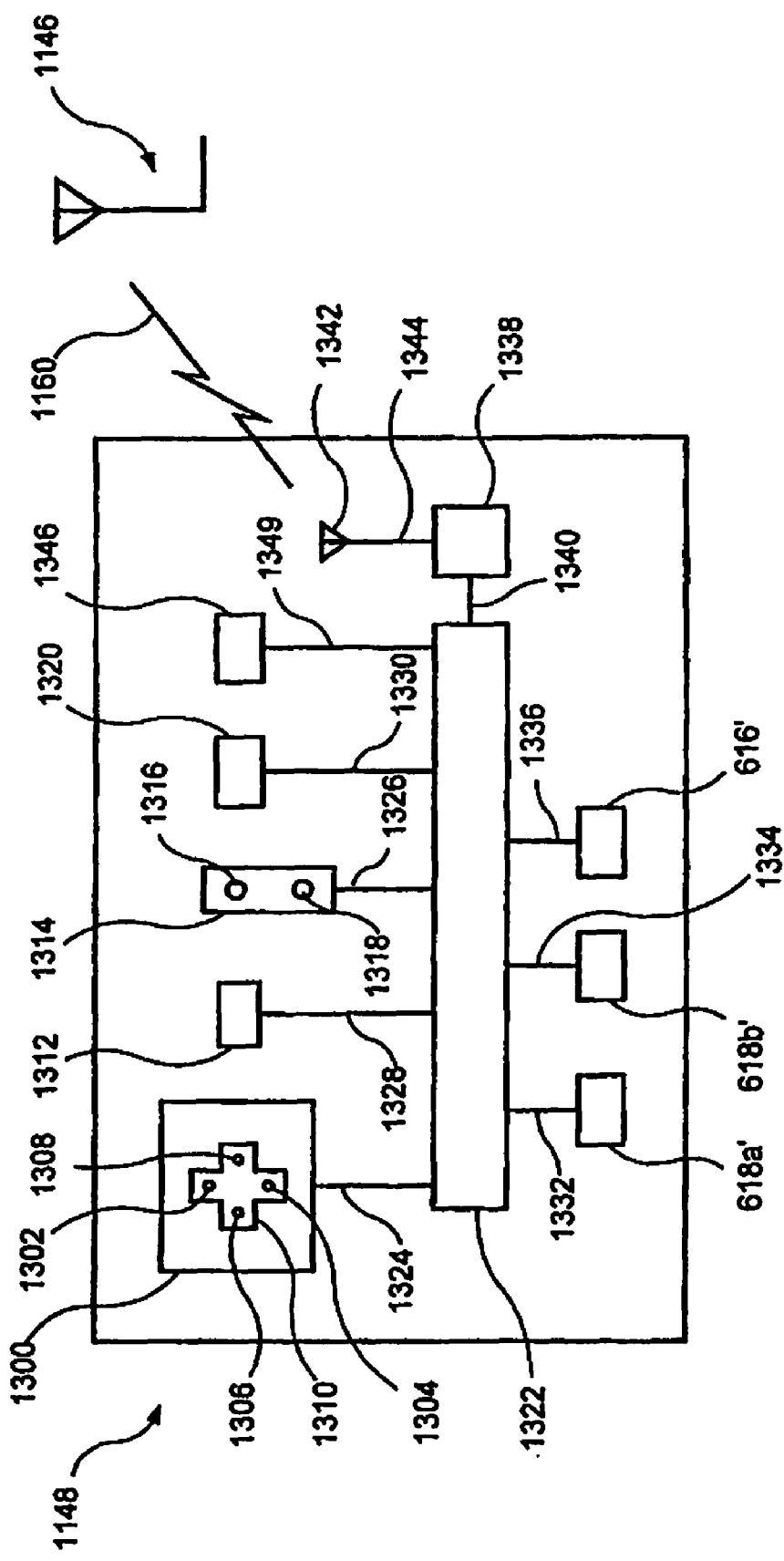
FIG. 18 is a schematic view of a wireless remote control unit of the electro-mechanical surgical system illustrated in FIG. 2.

Referring now to FIG. 18, there is seen a schematic view of the wireless RCU 1148. The wireless RCU 1148 includes a steering controller 1300 having a plurality of switches 1302, 1304, 1306, 1308 arranged under a four-way rocker 1310. The operation of the switches 1302, 1304, via a rocker 1310, controls the operation of first and second steering cables 634, 635 via a third motor 684. Similarly, the operation of the switches 1306, 1308, via the rocker 1310, controls the operation of the third and fourth steering cables 636, 637 via the fourth motor 692. It should be appreciated that the rocker 1310 and the switches 1302, 1304, 1306, 1308 are arranged so that the operation of the switches 1302, 1304 steers the flexible shaft 620 in the north-south direction and that the operation of the switches 1306, 1308 steers the flexible shaft 620 in the east-west direction. Reference herein to north, south, east and west is made to a relative coordinate system. Alternatively, a digital joystick, an analog joystick, etc. may be provided in place of the rocker 1310 and the switches 1302, 1304, 1306, 1308. Potentiometers or any other type of actuator may also be used in place of the switches 1302, 1304, 1306, 1308.

The wireless RCU 1148 further includes a steering engage/disengage switch 1312, the operation of which controls the operation of the fifth motor 696 to selectively engage and disengage the steering mechanism. The wireless RCU 1148 also includes a two-way rocker 1314 having first and second switches 1316, 1318 operable thereby. The operation of these switches 1316, 1318 controls certain functions of the electro-mechanical driver component 610 and any surgical instrument or attachment, such as the surgical device 11, attached to the flexible shaft 620 in accordance with the operating program or algorithm corresponding to the attached device 11. For example, operation of the two-way rocker 1314 may control the opening and closing of the first jaw 80 and the second jaw 50 of the surgical device 11. The wireless RCU 1148 is provided with yet another switch 1320, the operation of which may further control the operation of the electro-mechanical driver component 610 and the device 11 attached to the flexible shaft 620 in accordance with the operating program or algorithm corresponding to the attached device. For example, operation of the switch 1320 may initiate the advancement of the thrust plate 502 of the surgical device 11.

The wireless RCU 1148 includes a controller 1322, which is electrically and logically connected with the switches 1302, 1304, 1306, 1308 via line 1324, with the switches 1316, 1318 via line 1326, with switch 1312 via line 1328 and with switch 1320 via line 1330. The wireless RCU 1148 may include indicators 618a', 618b', corresponding to the indicators 618a, 618b of the front panel 615, and a display device 616', corresponding to the display device 616 of the front panel 615. If provided, the indicators 618a', 618b' are electrically and logically connected to the controller 1322 via respective lines 1332, 1334, and the display device 616' is electrically and logically connected to the controller 1322 via a line 1336. The controller 1322 is electrically and logically connected to a transceiver 1338 via line 1340, and the transceiver 1338 is electrically and logically connected to a receiver/transmitter 1342 via a line 1344. A power supply, for example, a battery, may be provided in the wireless RCU 1148 to power the same. Thus, the wireless RCU 1148 may be used to control the operation of the electro-mechanical driver component 610 and the device 11 attached to the flexible shaft 620 via the wireless link 1160.

The wireless RCU 1148 may include a switch 1346 connected to the controller 1322 via a line 1348. Operation of the switch 1346 transmits a data signal to the transmitter/receiver 1146 via a wireless link 1160. The data signal includes identification data uniquely identifying the wireless RCU 1148. This identification data is used by the controller 1122 to prevent unauthorized operation of the electro-mechanical driver component 610 and to prevent interference with the operation of the electro-mechanical driver component 610 by another wireless RCU. Each subsequent communication between the wireless RCU 1148 and the electro-mechanical device surgical 610 may include the identification data. Thus, the controller 1122 may discriminate between wireless RCUs and thereby allow only a single, identifiable wireless RCU 1148 to control the operation of the electro-mechanical driver component 610 and the device 11 attached to the flexible shaft 620.

Based on the positions of the components of the device attached to the flexible shaft 620, as determined in accordance with the output signals from the encoders 1106, 1108, the controller 1122 may selectively enable or disable the functions of the electro-mechanical driver component 610 as defined by the operating program or algorithm corresponding to the attached device. For example, for the surgical device 11, the firing function controlled by the operation of the switch 1320 is disabled unless the space or gap between second jaw 50 and first jaw 80 is determined to be within an acceptable range.

Figure 19:
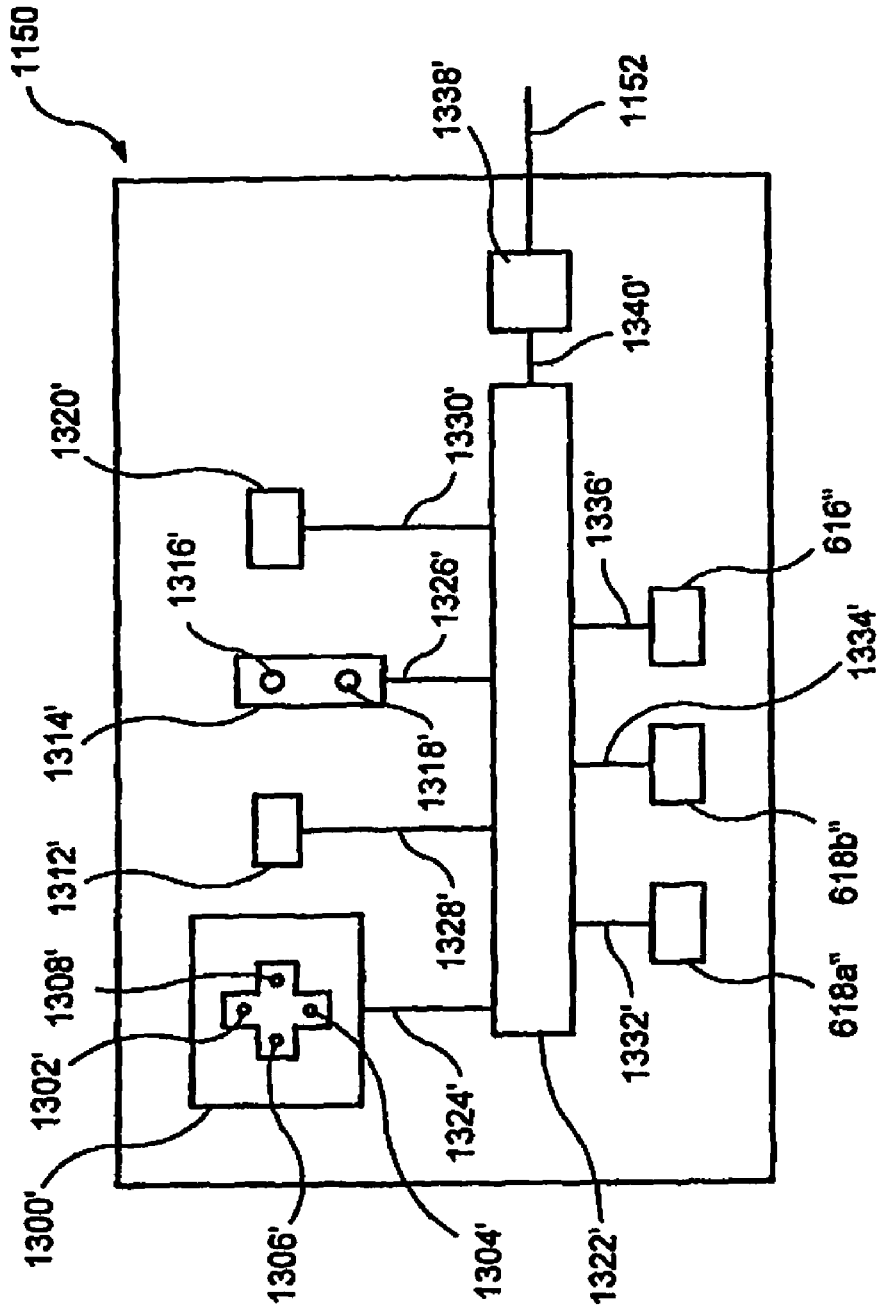
FIG. 19 is a schematic view of a wired remote control unit of the electro-mechanical surgical system illustrated in FIG. 2.

Referring now to FIG. 19, there is seen a schematic view of a wired RCU 1150. In the example embodiment, the wired RCU 1150 includes substantially the same control elements as the wireless RCU 1148 and further description of such elements is omitted. Like elements are indicated in FIG. 19 with an accompanying prime. It should be appreciated that the functions of the electro-mechanical driver component 610 and the device attached to the flexible shaft 620, e.g., the surgical device 11, may be controlled by the wired RCU 1150 and/or by the wireless RCU 1148. In the event of a battery failure, for example, in the wireless RCU 1148, the wired RCU 1150 may be used to control the functions of the electro-mechanical driver component 610 and the device attached to the flexible shaft 620.

As described hereinabove, the front panel 615 of the housing 614 includes the display device 616 and the indicators 618a, 618b. The display device 616 may include an alphanumeric display device, such as an LCD display device. The display device 616 may also include an audio output device, such as a speaker, a buzzer, etc. The display device 616 is operated and controlled by the controller 1122 in accordance with the operating program or algorithm corresponding to the device attached to the flexible shaft 620, e.g., the surgical device 11. If no surgical instrument or attachment is so attached, a default operating program or algorithm may be read by or selected by or transmitted to the controller 1122 to thereby control the operation of the display device 616 as well as the other aspects and functions of the electro-mechanical driver component 610. If surgical device 11 is attached to flexible shaft 620, the display device 616 may display, for example, data indicative of the gap between the second jaw 50 and the first jaw 80 as determined in accordance with the output signal of the encoders 1106, 1108, as more fully described hereinabove.

Similarly, the indicators 618a, 618b are operated and controlled by the controller 1122 in accordance with the operating program or algorithm corresponding to the device 11, attached to the flexible shaft 620, e.g., the surgical device 11. The indicator 618a and/or indicator 618b may include an audio output device, such as a speaker, a buzzer, etc., and/or a visual indicator device, such as an LED, a lamp, a light, etc. If the surgical device 11 is attached to the flexible shaft 620, the indicator 618a may indicate, for example, that the electro-mechanical driver component 610 is in a power ON state, and the indicator 618b may, for example, indicate whether the gap between the second jaw 50 and the first jaw 80 is determined to be within the acceptable range. It should be appreciated that although two indicators 618a, 618b are described, any number of additional indicators may be provided as necessary. Additionally, it should be appreciated that although a single display device 616 is described, any number of additional display devices may be provided as necessary.

The display device 616' and the indicators 618a', 618b' of the wired RCU 1150 and the display device 616" and the indicators 618a", 618b" of the wireless RCU 1148 are similarly operated and controlled by respective controller 1322, 1322' in accordance with the operating program or algorithm of the device attached to the flexible shaft 620.

As described above, the surgical device 11 may be configured to clamp, cut and staple a section of tissue. The operation of the surgical device 11 will now be described in connection with the removal of a cancerous or anomalous section of tissue in a patient's bowel, which is merely one type of tissue and one type of surgery that may be performed using the surgical device 11. Generally, in operation, after the cancerous or anomalous tissue in the gastrointestinal tract has been located, the patient's abdomen is initially opened to expose the bowel. In accordance with remote actuation provided by the electro-mechanical driver component 610, the first and second jaws 50, 80 of the surgical device 11 are driven into the open position by the first driver. As described above, the surgical device 11 may be initially maintained in the open position, thereby eliminating the need to initially drive the surgical device 11 into the open position. The tube of the bowel on a side adjacent to the cancerous tissue is placed adjacent to the first jaw 80. The second jaw 50 is in the swiveled position illustrated, for instance, in FIG. 9. By remote actuation, the first driver is engaged in reverse, and the second jaw 50 is caused to move towards the first jaw 80. Initially, the second jaw 50 moves while in the swiveled position until, when the jaws are in between the open and closed positions, the second jaw 50 is caused to swivel into alignment with the first jaw 80. Once the jaws are vertically aligned relative to each other, the first and second jaws are continued to be moved towards each other until the first jaw 80 closes against the second jaw 50, clamping the section of bowel therebetween. Once the bowel has been sufficiently clamped, the second driver is engaged, which causes the thrust plate (having the staple pusher and the knife mounted thereto) to move between a first position as illustrated in FIG. 5 and a second position as illustrated in FIG. 6, thereby cutting and stapling the bowel. The second driver is then engaged in reverse, which causes the staple pusher and the knife to move back into the first position as illustrated in FIG. 5. The first driver is then engaged to drive the first jaw 80 and the second jaw 50 of the surgical device 11 back into the open position. These steps are then repeated on the other side of the cancerous tissue, thereby removing the section of bowel containing the cancerous tissue, which is stapled on either end to prevent spilling of bowel material into the open abdomen.

More specifically, according to the example embodiment of the present invention, the surgical device 11 is coupled to the attachment coupling 626 of the electro-mechanical driver component 610 such that the first drive socket 180 engages the first drive shaft 630 of the electro-mechanical driver component 610 and the second drive socket 310 engages the second drive shaft 632 of the electro-mechanical driver component 610. Thus, rotation of the pinion 508a (hidden) is effected by rotation of the first drive socket 180 which is effected by rotation of the corresponding drive shaft 630 of the electro-mechanical driver component 610. Clockwise or counter-clockwise rotation of the pinion 508a is achieved depending on the direction of rotation of the motor 680. The rotation of the pinion 508b (hidden) is effected by rotation of the second drive socket 310 which is effected by rotation of the corresponding drive shaft 632 of the electro-mechanical driver component 610. Clockwise or counter-clockwise rotation of the pinion 508b is achieved depending on the direction of the motor 676.

When the surgical device 11 is in an initial closed position as illustrated in FIG. 4, the first motor 680 is operated in order to place the surgical device in the open position. Specifically, the first motor 680 corresponding to the first drive shaft 630 is activated, which engages the first drive socket 180, thereby causing the pinion 508a to turn in a first, e.g., counter-clockwise, rotation direction. Since circumferentially-disposed gear teeth of the pinion 508a are engaged with the circumferentially-disposed gear teeth 5291 of the spur gear 529a, the rotation of the pinion 508a causes the spur gear to rotate in a first, e.g., clockwise, direction which is opposite to the direction of rotation of the pinion 508a. The internal bore 5293 of the first spur gear 529a engages the end 5231 of the first worm 523a so as to cause the first worm 523a to rotate in the same direction as that of the first spur gear 529a, e.g., clockwise. The thread(s) 5233 of worm 523a engage the gear teeth 5221 of worm gear 522 so as to cause rotation of the worm gear 522 in a first, e.g., counter-clockwise when viewed from the top, direction. The internal bore of the worm gear 522 non-rotatably engages the screw 521, thereby causing the screw 521 to rotate in a first, e.g., counter-clockwise when viewed from the top, direction. The externally-disposed thread(s) 5214 of the screw 521 engage the threads of the internally-threaded bore 5051 of the swivel arm 509, thereby causing the swivel arm 509, and the anvil 505 attached thereto, to move in a downward direction, e.g., away from the first jaw 80. When the cam follower 571 within the swivel arm sleeve engages the curved portion of the channel 5052 of the swivel arm 509, the swivel arm 509, and the anvil 505 attached thereto, are caused to swivel out of alignment with the first jaw 80. Continuous operation of the motor in this manner eventually places the surgical device 11 in an open state, providing a space between the first jaw 80 and the second jaw 50, as illustrated in FIG. 3.

Next, a section of tissue is placed between the first jaw 80 and second jaw 50. The first motor 680 is operated in reverse in order to place the surgical device in the closed position. Specifically, the first motor 680 corresponding to the first drive shaft 630 is activated, which engages the first drive socket 180, thereby causing the pinion 508a to turn in a second, e.g., clockwise, direction of rotation. Since the circumferentially-disposed gear teeth (hidden) of the pinion 508a are engaged with the circumferentially-disposed gear teeth 5291 of the spur gear 529a, the rotation of the pinion 508a causes the spur gear 529a to rotate in a second, e.g., counter-clockwise, direction which is opposite to the direction of rotation of the pinion 508a. The internal bore 5293 of the first spur gear 529a is engaged with the end 5231 of the first worm gear 523a, such that the rotation of the first spur gear 529a causes the first worm 523a to rotate in the same direction as the first spur gear 529a, e.g., counter-clockwise. The thread(s) 5233 of the worm gear 523a are engaged with the worm gear teeth 5221 of worm gear 522, such that the rotation of the first worm 523a causes rotation of the worm gear 522 in a second, e.g., clockwise when viewed from the top, direction. The internal bore of the worm gear 522 is non-rotatably engaged with the screw 521, such that the rotation of the worm gear 522 causes the screw 521 to rotate in a second, e.g., clockwise when viewed from the top, direction. The externally-disposed thread(s) 5214 of the screw 521 are engaged with the threads of the internally-threaded bore 5051 of the swivel arm 509, such that the rotation of the screw 521 causes the swivel arm 509, and the anvil 505 attached thereto, to move in an upward direction, e.g., toward the first jaw 80. Again, the ball bearing 571 within the swivel arm sleeve 570 engages the channel 5052 of the swivel arm 509 such that, as the anvil 505 is moved vertically towards the first jaw 80, the swivel arm 509, and the anvil 505 attached thereto, is caused to swivel into alignment with the first jaw 80. The end 5181 of the pin 518 is inserted into an orifice 5057 of the anvil 505 and maintained in the inserted position in accordance with the bias of spring 524 to maintain the section of tissue between the jaws. Continuous operation of the motor in this manner eventually places the surgical device 11 in a closed state, as illustrated in FIG. 4, wherein the tissue is clamped between the first jaw 80 and the second jaw 50. In this closed state, the section of tissue to be stapled and cut is clamped between the staple holder 513 and the anvil 505.

To begin the stapling and cutting procedure, the second motor 676 is actuated in order to move the thrust plate 502 from a first, raised, e.g., retracted, position to a second, lowered, e.g., extended, position. Specifically, the second motor 676 corresponding to the second drive shaft 632 is activated. The second drive shaft 632 is engaged with the second drive socket 310, such that rotation of the second drive shaft 632 in a first direction, e.g., clockwise, causes the pinion 508b to rotate in a first, e.g., clockwise, direction of rotation. The engagement end of the pinion 508b is non-rotatably engaged with the internal bore 5294 of the coupling element 529b, such that the rotation of the pinion 508b causes the coupling element 529b to rotate in a first, e.g., clockwise, direction which is the same as the direction of rotation of the pinion 508b. The internal bore 5294 of the coupling element 529b is engaged with the end 5234 of the second worm gear 523b, such that the rotation of the coupling element 529b causes the second worm 523b to rotate in the same direction as that of the coupling element 529b, e.g., clockwise. The threads 5236 of the worm 523b are engaged with the worm gear teeth 5161 of the worm gear 516, such that rotation of the second worm 523b causes rotation of the worm gear 516 in a first, e.g., counter-clockwise when viewed from the top, direction. The thread(s) of the internally-threaded bore 5164 of the worm gear 516 are engaged with the thread(s) of the screw 504.

Because the screw 504 is non-rotatably coupled to the thrust plate 502, the screw 504 and the thrust plate 502 move together in a downward direction. Simultaneously, the threads 5236 of the worm 523b are engaged with the worm gear teeth 5171 of the worm gear 517, such that the rotation of the worm 523b causes rotation of the worm gear 517 in a first, e.g., clockwise when viewed from the top, direction. The thread(s) of the internally-threaded bore 5174 of the worm gear 517 engages the thread(s) of the screw 503. Because the screw 503 is non-rotatably coupled to the thrust plate 502, the screw 503 and the thrust plate 502 also move together in a downward direction. Thus, the thrust plate 502 is lowered in a continuous fashion, and the staple pusher 514 and the knife 519, which are mounted to the bottom surface 5022 of the thrust plate 502, are also lowered in a continuous fashion.

As the staple pusher 514 is lowered, the downwardly-disposed teeth 5143 of the staple pusher 514 are pushed through the slots 5132 of the staple holder 513. The staples 528, which are initially disposed within the slots 5132 of the staple holder 513, are pushed downwardly and out of the lower openings of the slots 5132 and through the clamped tissue until the prongs 5281 of the staples 528 contact corresponding staple guides 5053 of the anvil 505. The staple guides 5053 bend and close the prongs 5281 of the staples 528, thereby stapling the tissue. Simultaneously, the knife 519 mounted to the bottom surface 5022 of the thrust plate 502 passes through the longitudinally-disposed slot 5131 of the staple holder 513 until it contacts the knife pad 520 of the anvil 505, thereby cutting the clamped tissue.

Having performed a stapling and cutting procedure, the second motor 676 is actuated to move the thrust plate 502 from the second lowered position to the first raised position. Specifically, the second motor 676 corresponding to the second drive shaft 632 is activated, which is engaged with the second drive socket 310. The rotation of the second drive shaft 632 causes the pinion 508b to rotate in a second, e.g., counter-clockwise, direction. The engagement end of the pinion 508b is non-rotatably engaged with the internal bore 5294 of the coupling element 529b, such that this rotation of the pinion 508b causes the coupling element 529b to rotate in a second, e.g., counter-clockwise, direction. The internal bore 5294 of the coupling element 529b is also engaged with the end 5234 of the second worm 523b, such that the rotation of the coupling element 529b causes the second worm 523b to rotate in a second, e.g., counter-clockwise, direction. The thread(s) 5236 of the worm 523b are engaged with the circumferentially-disposed worm gear teeth 5161 of worm gear 516, such that the rotation of the worm 523b causes the rotation of the worm gear 516 in a second, e.g., clockwise when viewed from the top, direction. The thread(s) of the internally-threaded bore 5164 of the worm gear 516 are engaged with the thread(s) of the screw 504, and, because the screw 504 is non-rotatably coupled to the thrust plate 502, screw 504 and thrust plate 502 are together moved in an upward direction. Simultaneously, the thread(s) 5236 of the worm 523b engage the worm gear teeth 5171 of the worm gear 517, such that the rotation of the worm 523b causes rotation of the worm gear 517 in a second, e.g., counter-clockwise when viewed from the top, direction. The thread(s) of the internally-threaded bore 5174 of the worm gear 517 is engaged with the threads of the screw 503, and, because the screw 503 is non-rotatably coupled to the thrust plate 502, the screw 503 and the thrust plate 502 move together in an upward direction. Thus, the thrust plate 502 is raised in a continuous fashion, and the staple pusher 514 and the knife 519, which are mounted to the bottom surface 5022 of the thrust plate 502, are also raised in a continuous fashion to their initial retracted positions.

Having performed the cutting and stapling of the tissue and having returned the knife 519 to its retracted position, the first motor 680 is actuated to place the surgical device in the open position. Specifically, the first motor 680 corresponding to the first drive shaft 630 is activated. The first drive shaft 630 is engaged with the first drive socket 180, such that the rotation of the first drive shaft 630 causes the pinion 508a to rotate in a first direction of rotation, e.g., counter-clockwise. The gear teeth of the pinion 508a are engaged with the gear teeth 5291 of the spur gear 529a, such that the rotation of the pinion 508a causes the spur gear to rotate in a first, e.g., clockwise, direction. The internal bore 5293 of the first spur gear 529a is engaged with the end 5231 of the first worm 523a, such that the rotation of the first spur gear 529a causes the first worm 523a to rotate in the same direction as the first spur gear 529a, e.g., clockwise. The thread(s) 5233 of the worm gear 523a are engaged with the worm gear teeth 5221 of the worm gear 522, such that the rotation of the worm gear 523a causes the rotation of the worm gear 522 in a first, e.g., counter-clockwise when viewed from the top, direction. The internal bore of the worm gear 522 is non-rotatably engaged with the screw 521, such that the rotation of the worm gear 522 causes the screw 521 to rotate in a first, e.g., counter-clockwise when viewed from the top, direction. The externally-disposed thread(s) 5214 of the screw 521 are engaged with the thread(s) of the internally-threaded bore 5051 of the swivel arm 509, such that the rotation of the screw 521 causes the swivel arm 509, and the anvil 505 attached thereto, to move in an downward direction, e.g., away from the first jaw 80, and to swivel out of alignment with the first jaw 80. Thus, the second jaw 50 is separated from the first jaw 80, until the surgical device 11 is again in an open position, as illustrated in FIG. 3.

Thereafter, the surgical device 11 may be separated from the electro-mechanical driver component and replaced with another surgical device 11 so that the same clamping, cutting and stapling procedure may be performed on a different section of the tissue, e.g., on the opposite side of the anomalous or cancerous tissue. Once the second end of the bowel is also clamped, cut and stapled, the surgical device 11 may be separated from the electro-mechanical driver component 610. If necessary, an operator may discard the attachments or sterilize them for re-use.

It is noted that prior to actuation of the surgical device 11, a calibration procedure may be performed, either manually or automatically. Various calibration procedures that, according to several embodiments of the present invention, may be employed with the surgical device 11 are described in U.S. Provisional Patent Application No. 60/337,544, filed on Dec. 4, 2001, and U.S. patent application Ser. No. 10/309,532, filed on Dec. 4, 2002, which are expressly incorporated in their entirety herein by reference thereto.

According to the example embodiments of the present invention illustrated in FIGS. 8(a) through 8(e), the surgical device 11 may be non-reloadable in that the staple cartridge assembly 507 or some part thereof, e.g., the staple holder 513, may not be removable from the surgical device 11 by an operator to reload the surgical device 11 with a subsequent array of staples 523 and reuse the surgical device 11 for the same, or other, patient or for the same, or other, procedure. Thus, after the surgical device 11 has been actuated once to staple a section of tissue using the staples 528 in the staple holder 513, the surgical device 11 cannot be actuated again to staple another section of tissue using a new set of staples 528 or a new staple holder 513. By configuring the surgical device 11 so as to be non-reloadable, the risk of contamination or infection is reduced, since the surgical device 11 may not be intentionally or unintentionally used on two different patients and may not be re-used on a single patient. However, in accordance with one example embodiment of the present invention, the surgical device 11 may be reloadable. For example, in this example embodiment, the surgical device 11 may be configured such that certain components are removable from the surgical device 11 and replaceable with respect to the surgical device 11. For example, in accordance with one example embodiment, the staple cartridge assembly 507 is detachably attached to within the surgical device 11 and may be removed from the housing 506 after being used in order to be replaced by another staple cartridge assembly. The replaceable cartridge may be removable when the upper jaw 80 and the lower jaw 50 are in the fully open position to prevent the cartridge from being inadvertently removed when the upper jaw 80 and the lower jaw 50 are clamped onto a section of tissue to be cut and stapled. In one example embodiment, the staple cartridge assembly 507 or some part thereof, e.g., the staple holder 513, is slideable into and out of the surgical device 11, such that a user may slide a new staple cartridge assembly 507 or staple holder 513 having a new set of staples 528 into the surgical device 11 after the first set of staples 528 has been used. Alternatively, when the first set of staples 528 in the staple holder 513 has been used, the operator may replace the staples 528 in the same staple holder 513 and reuse the same staple holder 513. In one example embodiment, the pin 518 may be retractable out of the hole 5133 of the staple holder 513 such that the cartridge cap 515 may be removably or moveably connected to the housing 506.

In accordance with another example embodiment of the present invention, the surgical device 11 may provide limited reloadability. For example, the surgical device 11 may be configured to permit the staple holder 513 to be replaced once, so that the clamping, cutting and stapling operation may be performed twice on a single patient, e.g., on opposite sides of a cancerous section of tissue, but does not permit the staple holder 513 to be replaced more than twice.

In another example embodiment of the present invention, the surgical device 11 may be configured to maintain two sets of staples 528 within the staple holder 513, a first set of which is used on one side of a cancerous section of tissue and a second set of which is used on the other side of the cancerous section of tissue. It should be understood that the surgical device 11 may be configured for any number of uses and that usage may be determined in accordance with the usage data 1184. That is, the memory module 501 and/or 5011 may be configured to store data representing the number of times that the surgical device 11 is reloaded. Thus, in accordance with the operating program, the electro-mechanical driver component 610 may limit the number of times that a reloaded surgical device 11 may be fired in accordance with the usage information stored in the memory module 501 and/or 5011.

A surgical device 11 that is configured to be reloadable may be operated in a similar manner to the non-reloadable surgical device 11 described above. However, the reloadability of the surgical device 11 permits the operator to perform additional steps during the operation of the surgical device 11. For example, once the surgical device 11 is initially placed in the open position, the staple holder 513 may be accessed by the operator and may be inspected to determine whether the staples 528 are ready for the procedure and/or whether the need exists to replace the staple holder 513 with a more suitable staple holder 513. Similarly, once a clamping, cutting and stapling operation has been performed and the set of staples 528 has been used, the staple holder 513 may be accessed by the operator again in order to replace the staple holder 513 with another staple holder 513 or to insert another set of staples 528 into the same staple holder 513.

According to the example embodiments of the present invention illustrated in FIGS. 8(a) and 8(b), the surgical device 11 may be configured to operate in more than one range of operation. This feature may provide the advantage that sections of tissue having different thicknesses may be more appropriately accommodated by the surgical device 11. Various examples of such a feature are described in, e.g., U.S. Provisional Patent Application No. 60/346,656, filed on Jan. 8, 2002, and U.S. patent application Ser. No. 10/094,051, filed on Mar. 8, 2002, which are expressly incorporated herein in their entirety by reference thereto.

The surgical device 11, according to various example embodiments thereof, may also employ or be employed with various operating programs for operating the surgical device 11. Examples of such operating programs are described in, e.g., U.S. Provisional Patent Application No. 60/346,656, filed on Jan. 8, 2002, and U.S. patent application Ser. No. 10/094,051, filed on Mar. 8, 2002, which as set forth above are expressly incorporated herein in their entirety by reference thereto.

One problem of conventional surgical devices is that they may limit the approach angle at which the device is used. As previously described, conventional surgical devices typically employ an instrument shaft that is perpendicular to the section of tissue to be cut or stapled. When a conventional surgical device is employed corporally, e.g., inside the body of a patient, the device is limited to a single approach angle for cutting and stapling the section of tissue.

By contrast, the surgical device 11 may not limit the approach angle at which the device is used. As previously described, the surgical device 11, according to various example embodiments thereof, includes drive shafts 630 and 632 that are coupled to the first jaw 80 at an angle, e.g., perpendicular, to the plane of movement of the first jaw 80 relative to the second jaw 50. Thus, when the surgical device 11 is employed intracorporally, e.g., inside the body of a patient, the surgical device 11 may not be limited to a single approach angle. Instead, a variety of approach angles may be employed, which may enable an operator to more effectively use the surgical device on various sections of tissue.

Another problem of conventional surgical devices is that they may be difficult to maneuver within the body of a patient. For example, when a conventional surgical device is employed to clamp or staple a section of tissue that is not easily maneuverable, the surgical device must be maneuvered instead. For example, in the case of a section of gastro-intestinal tissue located adjacent to the anal stump, the section of tissue may not be maneuverable prior to or during performance of the operation. A conventional surgical device cannot be employed in such a location, because the approach angle required to be used by an operator may interfere with the pelvis of the patient. Furthermore, conventional surgical devices may not be positionable satisfactorily in such a location because the jaws of the surgical device, when in the open position, require a large space and are prevented from being positioned by the close proximity of the surrounding tissues inside the patient's body.

In contrast, the surgical device 11 according to various example embodiments thereof, may be less difficult to maneuver within the body of a patient. For example, in the above-described case of a section of gastro-intestinal tissue located adjacent to the anal stump, the surgical device 11 may be positioned at the very end of the section of gastro-intestinal tissue nearest the anus. Thus, the angled, e.g., perpendicular, arrangement of the drive shafts 630 and 632 relative to the plane of movement of the first jaw 80 relative to the second jaw 50 may improve the maneuverability of the surgical device 11 within the body of the patient. Furthermore, the swivelable jaw of the present invention reduces the space that is required by the jaws when in the open position. When the surgical device 11 of the present invention is in the fully open position, only the first jaw 80 is positioned at the distal end of the surgical device 11, the second jaw 50 being swiveled out of alignment with the first jaw 80. Using the example surgical procedure of clamping, cutting and stapling a section of tissue at the anal stump, the first jaw 80 may be positioned closer to the anal stump than may be possible with conventional surgical devices because the second jaw 50 is swiveled away from the tissue located immediately adjacent to the anal stump. When the surgical device is moved into the closed position, the second jaw 50 is gradually swiveled into alignment with the first jaw 80. When the second jaw 50 is eventually aligned with the first jaw 80, the space required by the two jaws is less than would have been required had the two jaws been aligned in the fully open position. In this manner, the surgical device 11 may provide improved positionability within a patient's body.

Thus, the several aforementioned objects and advantages of the present invention are most effectively attained. Those skilled in the art will appreciate that numerous modifications of the exemplary example embodiments described hereinabove may be made without departing from the spirit and scope of the invention. Although various exemplary example embodiments of the present invention have been described and disclosed in detail herein, it should be understood that this invention is in no sense limited thereby and that its scope is to be determined by that of the appended claims.

What is claimed is:

1. A surgical device, comprising:
a first jaw including a sleeve attached thereto and defining a first longitudinal axis that lies in a first plane having a fixed position with respect to the first jaw; and
a second jaw including an arm configured to move longitudinally within and relative to the sleeve, the second jaw coupled to and moveable relative to the first jaw between a closed position and an intermediate open position, the second jaw defining a second longitudinal axis that, when the second jaw is in the closed position or in the intermediate open position, the second longitudinal axis lies substantially within the first plane, the sleeve and the arm including a camming arrangement that is configured to move the second jaw at least between the intermediate open position and a fully open position by rotating the second jaw with respect to the first jaw about an axis substantially transverse to the first and second longitudinal axes and lying within the first plane, wherein in the fully opened position, at least one of the first jaw and the second jaw is not disposed within the first plane.

2. The device according to claim 1, wherein, between the intermediate open position and the fully opened position, the second jaw is further moveable relative to the first jaw toward an orientation substantially transverse to the first plane.

3. The device according to claim 2, further comprising a first driver configured to cause relative movement of the first jaw and the second jaw.

4. The device according to claim 3, further comprising an electromechanical driver configured to rotate the first rotatable drive shaft.

5. The device according to claim 2, wherein the first driver is configured to engage a first rotatable drive shaft rotatable about a rotation axis arranged at an angle that includes or is between parallel and perpendicular correspondence to the first plane.

6. The device according to claim 5, wherein the rotation axis of the first rotatable drive shaft is perpendicular to the first plane of the first and second jaws.

7. The device according to claim 5, wherein the first rotatable drive shaft is rotated in a first direction to effect extending of the jaws and rotated in a second direction opposite to the first direction to effect closing of the jaws.

8. The device according to claim 5, further comprising an electromechanical driver including the first rotatable drive shaft adapted to drive the first driver and a second rotatable drive shaft adapted to drive a second driver.

9. The device according to claim 2, wherein the first driver includes at least a spur gear, a worm and a worm gear in turning and gearing relationship with each other, and an externally-threaded screw fixedly connected at one end to the worm gear and in engagement with an internally-threaded bore of the second jaw, the rotation of the gears thereby causing relative movement of the first jaw and the second jaw.

10. The device according to claim 9, wherein the internally threaded bore of the second jaw is disposed within an arm, the arm configured to move longitudinally within and relative to a sleeve attached to the first jaw.

11. The device according to claim 1, further comprising: a surgical member disposed within the first jaw; and a second driver configured to cause relative movement of the surgical member in a direction parallel to the first plane.

12. The device according to claim 11, wherein the second driver is configured to engage a second drive shaft rotatable about a rotation axis arranged in perpendicular correspondence to the first plane.

13. The device according to claim 12, wherein the second rotatable drive shaft is rotated in a first direction to extend the surgical member and rotated in a second direction opposite to the first direction to retract the surgical member.

14. The device according to claim 11, wherein the second driver is configured to engage a second drive shaft rotatable about a rotation axis arranged in parallel correspondence to the first plane.

15. The device according to claim 11, wherein the surgical member includes one of a cutting element, a stapling element and a thrust plate to which is mounted a cutting element and a stapling element.

16. The device according to claim 11, wherein the second driver includes at least a spur gears and a worm in turning and gearing relationship with each other and with a pair of additional worm gears, each of the pair of additional worm gears having a centrally-disposed, internally-threaded bore in engagement with one of a pair of externally-threaded screws fixedly connected the surgical member, the rotation of the gears thereby causing relative movement of the surgical member.

17. The device according to claim 1, wherein the camming arrangement includes a channel disposed along at least one of the arm and the sleeve, and a cam follower slidably disposed within the channel, wherein the channel includes a helical portion.

18. A surgical device, comprising:
a first rotatable drive shaft rotatable about a rotation axis;
a first jaw defining a first longitudinal axis that lies in a first plane having a fixed position with respect to the first jaw;
a second jaw coupled to the first jaw, the second jaw moveable relative to the first jaw by rotation of the first drive shaft between a closed position and an intermediate open position, the second jaw defining a second longitudinal axis that, when the second jaw is in the closed position or in the intermediate open position, the second longitudinal axis lies substantially within the first plane, the second jaw further moveable between the intermediate open position and a fully opened position by rotating the second jaw with respect to the first jaw about an axis substantially transverse to the first and second longitudinal axes and laying within the first plane;

a surgical member disposed within the first jaw; and an electromechanical driver including the first rotatable drive shaft adapted to drive a first driver and a second rotatable drive shaft adapted to drive a second driver, wherein the second driver is configured to cause relative movement of the surgical member in a direction parallel to the first plane, wherein the second driver includes at least a spur and a worm gear in turning and gearing relationship with each other and with a pair of additional worm gears each of the pair of additional worm gears having a centrally-disposed, internally-threaded bore in engagement with one of a pair of externally-threaded screws fixedly connected to the surgical member, wherein a rotation of the gears causes relative movement of the surgical member, wherein the internally-threaded bore is disposed within an arm of the second jaw, the arm configured to move longitudinally within and relative to a sleeve attached to the first jaw.

19. The device according to claim 18, wherein, in the fully opened position, at least one of the first jaw and the second jaw is not disposed within the first plane.

20. The device according to claim 19, wherein the second jaw includes an arm and the first jaw includes a sleeve attached thereto, the arm configured to move longitudinally within and relative to the sleeve, the sleeve and the arm including a camming arrangement that is configured to move the second jaw at least between the intermediate open position and the fully open position.

21. The device according to claim 18, wherein, between the intermediate open position and the fully opened position, the second jaw is further moveable relative to the first jaw toward an orientation substantially transverse to the first plane.

22. The device according to claim 21, further comprising a first driver configured to cause relative movement of the first jaw and the second jaw.

23. The device according to claim 21, wherein the first driver is configured to engage a drive shaft rotatable about a rotation axis arranged at an angle that includes or is between parallel and perpendicular correspondence to the first plane.

24. The device according to claim 21, wherein the first driver includes at least a spur gear, a worm and a worm gear in turning and gearing relationship with each other, and an externally-threaded screw fixedly connected at one end to the worm gear and in engagement with an internally-threaded bore of the second jaw, the rotation of the gears thereby causing relative movement of the first jaw and the second jaw.

25. The device according to claim 21, further comprising an electromechanical driver including the first rotatable drive shaft adapted to drive the first driver and a second rotatable drive shaft adapted to drive a second driver.

26. The device according to claim 18, wherein the second driver is configured to engage a second drive shaft rotatable about a rotation axis arranged in substantially perpendicular correspondence to the first plane.

27. The device according to claim 18, wherein the second driver is configured to engage a second drive shaft rotatable about a rotation axis arranged in substantially parallel correspondence to the first plane.

28. The device according to claim 18, wherein the surgical member includes one of a cutting element, a stapling element and a thrust plate to which is mounted a cutting element and a stapling element.

29. The device according to claim 18, further comprising an electromechanical driver configured to rotate the first rotatable drive shaft.

30. The device according to claim 18, wherein the rotation axis of the first rotatable drive shaft is perpendicular to the first plane of the first and second jaws.

31. The device according to claim 18, wherein the first rotatable drive shaft is rotated in a first direction to effect extending of the jaws and rotated in a second direction opposite to the first direction to effect closing of the jaws.

32. The device according to claim 18, wherein the second rotatable drive shaft is rotated in a first direction to extend the surgical member and rotated in a second direction opposite to the first direction to retract the surgical member.

33. The device according to claim 18, wherein the second driver includes at least a spur gears and a worm in turning and gearing relationship with each other and with a pair of additional worm gears each of the pair of additional worm gears having a centrally-disposed, internally-threaded bore in engagement with one of a pair of externally-threaded screws fixedly connected the surgical member, the rotation of the gears thereby causing relative movement of the surgical member.

34. The device according to claim 18, wherein the camming arrangement includes a channel disposed along at least on of the arm and the sleeve, and a cam follower slidably disposed within the channel, wherein the channel includes a helical portion.

35. A method of operating a surgical device, comprising the step of:

moving a second jaw defining a second longitudinal axis relative to a first jaw defining a first longitudinal axis between a closed position and an intermediate open position wherein the first longitudinal axis lies in a first plane having a fixed position with respect to the first jaw and when the second jaw is in the closed position or in the intermediate open position, the second longitudinal axis lies substantially within the first plane, wherein the first jaw and the second jaw include a camming arrangement;

moving the second jaw relative to the first jaw between the intermediate open position and a fully opened position by rotating the second jaw with respect to the first jaw about an axis substantially transverse to the first and second longitudinal axes and lying within the first plane; and engaging a camming arrangement when the first and second jaws are moved between the intermediate position and the fully open position.

36. The method according to claim 35, wherein in the fully opened position, at least one of the first jaw and the second jaw is not disposed within the first plane.

37. The method according to claim 36, wherein the second jaw includes an arm and the first jaw includes a sleeve attached thereto, the arm configured to move longitudinally within and relative to the sleeve, the sleeve and the arm including a camming arrangement that is configured to move the second jaw at least between the intermediate open position and the fully open position.

38. The method according to claim 35, further comprising the step of:

rotating a first drive shaft about a rotation axis, the first drive shaft configured to move the second jaw between the closed, intermediate open and fully opened positions.

39. The method according to claim 38, further comprising the steps of:
rotating a second drive shaft; and
moving a surgical member disposed within the first jaw in a direction parallel to the first plane and in accordance with the rotation of the second rotatable drive shaft.

40. The method according to claim 39, wherein the surgical member includes at least one of a cutting element and a stapling element.

41. The method according to claim 38, wherein the first rotatable drive shaft is rotated by an electromechanical driver.

42. The method according to claim 38, wherein the second rotatable drive shaft is rotated by an electromechanical driver.

43. The method according to claim 35, wherein the camming arrangement includes a channel disposed along at least one of the arm and the sleeve, and a cam follower disposed within the channel, wherein the channel includes a helical portion.

* * * * *